(12) United States Patent
Glen et al.

(10) Patent No.: US 11,160,644 B2
(45) Date of Patent: Nov. 2, 2021

(54) DEVICES AND METHODS FOR ORAL HYGIENE

(71) Applicant: PerioNovum LLC, Bala Cynwyd, PA (US)

(72) Inventors: Jeffrey D. Glen, Bala Cynwyd, PA (US); Joshua C. Glen, Bala Cynwyd, PA (US)

(73) Assignee: PERIONOVUM LLC, Bala Cynwyd, PA (US)

( * ) Notice: Subject to any disclaimer, the term of this patent is extended or adjusted under 35 U.S.C. 154(b) by 113 days.

(21) Appl. No.: 16/459,301

(22) Filed: Jul. 1, 2019

(65) Prior Publication Data

US 2020/0000564 A1    Jan. 2, 2020

Related U.S. Application Data

(60) Provisional application No. 62/693,332, filed on Jul. 2, 2018.

(51) Int. Cl.
*A61C 17/22* (2006.01)
*A61C 17/00* (2006.01)
(Continued)

(52) U.S. Cl.
CPC ............ *A61C 17/005* (2013.01); *A46B 9/045* (2013.01); *A46B 11/0003* (2013.01);
(Continued)

(58) Field of Classification Search
CPC ....... A61C 17/005; A61C 17/00; A61C 15/00; A61C 9/0006; A61C 19/06; A61C 19/063; A61C 19/066; A61C 17/228; A46B 9/045; A46B 11/0003

USPC .......... 433/3, 97, 141, 214, 216, 217.1, 229; 15/167.2, 104.93, 104.94; 601/139; 401/9, 10, 11

See application file for complete search history.

(56) References Cited

U.S. PATENT DOCUMENTS 5,175,901 A  *  1/1993  Rabinowitz ............ A46B 9/045
                                                    15/167.1
8,292,624 B2 * 10/2012  Gallagher, Jr. .... A46B 11/0003
                                                    433/216

(Continued)

FOREIGN PATENT DOCUMENTS

AU        2015407320 B2     3/2017
WO    WO 2009/157932 A1    12/2009
(Continued)

OTHER PUBLICATIONS

Translation of Yoo document (Year: 2015).*
(Continued)

*Primary Examiner* — Heidi M Eide
(74) *Attorney, Agent, or Firm* — Knobbe Martens Olson & Bear LLP

(57) ABSTRACT

This application relates to oral hygiene and/teeth cleaning devices and associated methods. The devices can be configured to have a shape that allows all or substantially all of a user's teeth to be cleaned at once. In some embodiments, the devices are configured to be useable, for example, without access to water or a bathroom. The devices can be used to freshen up and clean the user's mouth on-the-go. In some embodiments, the devices are disposable.

19 Claims, 26 Drawing Sheets

(51) Int. Cl.
*A61C 19/06* (2006.01)
*A61Q 11/00* (2006.01)
*A46B 9/04* (2006.01)
*A46B 11/00* (2006.01)
*A61C 15/00* (2006.01)

(52) U.S. Cl.
CPC .......... *A61C 17/228* (2013.01); *A61C 19/066* (2013.01); *A61Q 11/00* (2013.01); *A61C 15/00* (2013.01)

(56) References Cited

U.S. PATENT DOCUMENTS

| | | | | |
|---|---|---|---|---|
| 8,636,677 | B2 * | 1/2014 | Van Der Rijt | A61C 17/228 601/139 |
| 2004/0074035 | A1 * | 4/2004 | Huang | A46B 9/005 15/167.2 |
| 2008/0233541 | A1 * | 9/2008 | De Vreese | A61C 19/063 433/216 |
| 2008/0280251 | A1 * | 11/2008 | Gallagher | A46B 11/0003 433/80 |
| 2009/0208898 | A1 * | 8/2009 | Kaplan | A61C 17/028 433/80 |
| 2009/0276972 | A1 * | 11/2009 | Dugan | A61C 17/349 15/167.2 |
| 2012/0202172 | A1 * | 8/2012 | Raghuprasad | A61C 19/063 433/217.1 |
| 2012/0321369 | A1 | 12/2012 | Herr et al. | |
| 2013/0067665 | A1 * | 3/2013 | Sowinski | A61C 17/228 15/4 |
| 2014/0093836 | A1 * | 4/2014 | Wolpo | A61N 1/0548 433/32 |
| 2014/0123421 | A1 * | 5/2014 | Minano Fernandez | A46B 9/06 15/110 |
| 2014/0272761 | A1 * | 9/2014 | Lowe | A61C 17/005 433/24 |
| 2015/0282910 | A1 * | 10/2015 | Furdui-Carr | A46B 9/04 15/22.2 |
| 2016/0135581 | A1 * | 5/2016 | Pai | A46B 5/0095 433/216 |
| 2016/0206415 | A1 * | 7/2016 | Kraft | A61C 17/3481 |
| 2017/0367801 | A1 * | 12/2017 | Fitzgerald | A61C 17/228 |
| 2018/0098832 | A1 * | 4/2018 | Pierce | A61C 17/222 |
| 2018/0368957 | A1 * | 12/2018 | Hyun | A61C 17/228 |
| 2019/0183619 | A1 * | 6/2019 | Reizenson | A61C 1/0084 |

FOREIGN PATENT DOCUMENTS

| | | | | |
|---|---|---|---|---|
| WO | WO 2015/024023 A1 | 2/2015 | | |
| WO | WO-2015072676 A1 * | 5/2015 | | A46B 9/045 |
| WO | WO 2016/115276 A1 | 7/2016 | | |

OTHER PUBLICATIONS

"Is Swallowing Toothpaste Dangerous?" Islington Dental Clinic, Islington Dental Clinic, Feb. 21, 2020, islingtondentalclinic.com/news-ls+swallowing+toothpaste+dangerous%3F-2072. (Year: 2020).*
International Search Report for International Application No. PCT/US2019/040197 dated Sep. 24, 2019.

* cited by examiner

DEVICES AND METHODS FOR ORAL HYGIENE

RELATED APPLICATION(S)

This application claims priority to U.S. Provisional Patent Application No. 62/693,332, filed Jul. 2, 2018, which is incorporated herein by reference. Any and all applications for which a foreign or domestic priority claim is identified in the Application Data Sheet as filed with the present application are hereby incorporated by reference under 37 CFR 1.57.

BACKGROUND

Field

This application relates to oral healthcare, and in particular, to devices and methods for maintaining oral hygiene, cleaning teeth, and/or freshening the mouth.

Description

Oral hygiene is important for many reasons, including, for example, preventing dental decay and gum disease, and keeping breath fresh. Generally, people brush, floss, and use mouthwash to keep their mouth and teeth clean.

SUMMARY

Foods that contain sugar can attach to teeth and start the process of decay. Biofilm can develop within hours and can lead to decay and other gum-related health issues. Any removal of the decay-causing bacteria helps reduce dental decay and any disruption of the biofilm on the tooth surfaces and below the gum can make a significant impact on the health of the gums. Additionally, halitosis (bad breath) can have many negative effects on a person, such as social embarrassment.

Presently, there is a need for oral hygiene when there is no close proximity to safe drinking water. Many people use public restrooms to brush or freshen their teeth. However, public restrooms are known to contain germs and bacteria, such as fecal matter, that could be detrimental to a person's health. An occurrence known as toilet plume can spread germs and bacteria throughout a public restroom. Additionally, many people around the world do not have any access to clean water, and some do not have access to any water at all. This is prevalent in third world countries and is also common when military personnel are deployed. Additionally, people may not have access to water in national disaster situations, or during camping or travel.

There is also a need for oral hygiene that is quick, efficient, and convenient. For example, most professionals work long hours and do not have time to go home or find a restroom between meetings or after work before social activities. Moreover, for the reasons mentioned above, it is better to avoid brushing one's teeth in a public restroom at all (e.g., due to toilet plume and other unsanitary conditions in public restrooms). Additionally, frequent travelers, campers, and people who must wear plastic trays all day (e.g., invisalign users) need devices and methods for oral hygiene that are quick, efficient, and convenient to be able to wear the trays for the required period of time.

The traditional paradigm of brushing twice a day (morning and night) is not sufficient to maintain healthy teeth. People need to be able to clean their teeth on-the-go (e.g., between regular brushings) to act as a supplement for good oral care.

This application describes oral hygiene devices that can be used to maintain oral hygiene, clean teeth, and/or freshen one's breath or mouth. The oral hygiene devices can be configured to be used without water, such that they can quickly and easily be used while on-the-go or where access to water is inconvenient or unavailable. In some embodiments, the oral hygiene devices can be manufactured for relatively low costs such that the oral hygiene device can be used in a disposable manner. In some embodiments, the oral hygiene device herein can be used for people that lack dexterity (e.g., within a nursing home or for people who are bedridden).

The oral hygiene devices can be configured such that they can be used quickly. For example, the oral hygiene devices may be configured to fit over all or substantially all of a user's upper and or lower teeth such that all or substantially all of the user's upper and or lower teeth can be cleaned by the device simultaneously. This can reduce the overall time required to use the device.

In some embodiments, the oral hygiene devices can be used as a supplement to traditional tooth cleaning methodologies of brushing, flossing, and mouthwash. For example, the oral hygiene devices can be configured for use in between meals (or whenever desired) to clean and freshen one's mouth when access to brushing, flossing, and mouthwash may not be available. The oral hygiene device can advantageously be configured to be used without water, allowing them to be used nearly anywhere at any time.

In a first aspect, an oral hygiene device comprises: a U-shaped body comprising a first material, the U-shaped body comprising a channel configured to receive a user's upper or lower teeth, the U-shaped body comprising a first material; one or more teeth cleaning features over molded onto the U-shaped body, the one or more teeth cleaning features made of a second material that is softer than the first material and the one or more teeth cleaning features comprising a plurality of ribs disposed within the channel, at least some of ribs comprising a finger that extends at an angle of approximately 45 degrees with respect to a bottom wall of the channel, and one or more reservoirs holding a dab configured to freshen the user's mouth, wherein the dab is configured to be useable without water; wherein the oral hygiene device is configured to be useable without access to water or a restroom.

The oral hygiene device can include one or more of the following features in any combination: wherein the first material comprises polypropylene, and wherein the second material comprises a thermoplastic elastomer (TPE) or a thermoplastic polyurethane (TPU); wherein the second material comprises a Shore A hardness between 80 and 90; one or more tongue cleaning features extending from a bottom surface of the bottom wall of the channel of the body; wherein the one or more tongue cleaning features comprise one or more ridges formed of the second material; wherein the reservoirs are configured to extend through the bottom wall of the U-shaped body; wherein the reservoirs are configured to extend at least 0.5 mm above and below the bottom wall of the U-shaped body; wherein the reservoirs comprise openings extending therethrough to facilitate release of the dab; wherein the dab comprises a formulation that is safe to swallow; wherein the dab comprises fluoride; wherein the one or more teeth cleaning features are configured to contact at least 50%, at least 60%, at least 75%, at least 80%, or at least 90% of the user's upper or lower teeth simultaneously; and/or a handle extending from the U-shaped body.

In another aspect, a method for freshening or cleaning a user's mouth is disclosed, the method comprising: inserting an oral hygiene device into a user's mouth, the oral hygiene device comprising a U-shaped body having a channel formed therein; positioning the oral hygiene device such that the user's upper or lower teeth are positioned within the channel; moving the oral hygiene device side to side and front to back to clean the user's upper or lower teeth, wherein moving the oral hygiene device distributes a formulation from dabs in reservoirs of the oral hygiene device; flipping the oral hygiene device such that the other of the user's upper or lower teeth are positioned within the channel; and moving the oral hygiene device side to side and front to back to clean the other of the user's upper or lower teeth.

The method can include one or more of the following features, in any combination: wherein the method is performed without access to water or a restroom; cleaning the user's tongue with one or more tongue cleaning features of the oral hygiene device by running the one or more tongue cleaning features of the oral hygiene device over the tongue; wherein the oral hygiene device is configured to contact at least 50%, at least 60%, at least 75%, at least 80%, or at least 90% of the user's upper or lower teeth simultaneously; disposing of the oral hygiene device after use; swallowing the formulation, and wherein the formulation is safe to swallow; and/or wherein the formulation comprises fluoride.

In another aspect, an oral hygiene device is disclosed that comprises: a U-shaped body configured in size and shape to be positioned over a user's upper or lower teeth during use; and one or more teeth cleaning features extending from the body and configured to clean the user's teeth.

The oral hygiene device can include one or more of the following features in any combination: wherein the one or more teeth cleaning features are configured to contact at least 50%, at least 60%, at least 75%, at least 80%, or at least 90% of the user's teeth simultaneously; wherein the one or more teeth cleaning features comprise at least one of bristles, foam, rubberized fingers, ribs, and textured surfaces; wherein the one or more teeth cleaning features comprise ribs, and wherein the shape of each rib is adapted to follow the contour of the teeth which the rib will overlie during use of the device; wherein the ribs are positioned in a channel of the body; wherein the body comprises a first material and the ribs comprise a second material that is softer than the first material; wherein the device is formed with a two-step injection molding process; wherein the shape of at least some of the ribs is adapted to clean a gum line of the user; wherein at least some of the ribs include an angled finger configured to contact the gum at an angle; wherein the body comprises at least one hinge such that the device can be transitioned between an open configuration and a closed configuration; wherein the open configuration is configured to allow the device to fit within a generally linear package, and the closed configuration is generally U-shaped; wherein the device includes two hinges; wherein the at least one hinge is a living hinge; at least one locking mechanism configured to secure the device in the closed configuration; one or more beads of mouthwash, toothpaste, freshening gel or paste, desensitizing gel or paste, or whitening gel or paste; wherein the one or more beads are received within one or more pockets; wherein the one or more beads dissolve within the mouth during use; wherein the device is configured to be used without water; wherein the device is configured for a single use; wherein the device is disposable; a handle for manipulating the device; and/or wherein the handle comprises a tab configured to extend out of the mouth between the user's lips.

BRIEF DESCRIPTION OF THE DRAWINGS

The features of the present disclosure will become apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 12A illustrates a top view in a straight configuration, FIG. 12B illustrates an inside view in a straight configuration, and FIG. 12C illustrates a top view in a bent configuration.

Figure 1A:
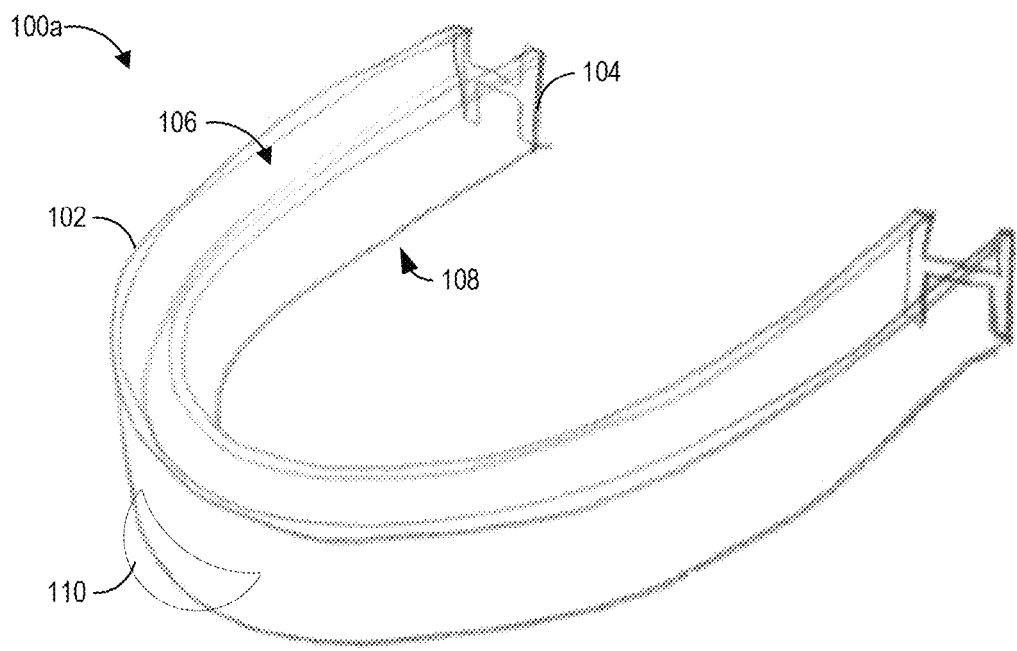
FIG. 1A is a perspective view of an embodiment of an oral hygiene device that includes an H-shaped cross-section.

Various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

This application relates to oral hygiene and/or teeth cleaning devices and associated methods. The oral hygiene devices can be configured to have a shape that allows all or substantially all of a user's teeth (for example, all or substantially all of a user's upper teeth and/or all or substantially all of a user's lower teeth) to be cleaned at once. In some embodiments, the oral hygiene devices are configured to be useable, for example, without access to water or a bathroom. Thus, the oral hygiene devices can be used to freshen and clean the user's mouth on-the-go. In some embodiments, the oral hygiene devices are disposable.

The features, aspects, and advantages of the present application will now be further described with reference to the drawings of several embodiments, which are intended to be within the scope of the embodiments disclosed herein. These and other embodiments will become readily apparent to those skilled in the art from the following detailed description of the embodiments having reference to the attached figures, the development not being limited to any particular embodiment herein disclosed.

FIG. 1A is a perspective view of an embodiment of an oral hygiene device 100a. The oral hygiene device 100a can be useable to freshen a user's mouth and/or clean the user's teeth. The oral hygiene device 100a includes a body 102. In the illustrated embodiment, the body 102 is generally U-shaped (e.g., comprises a general U-shape when viewed from above or below). The generally U-shaped body 102 can be configured to follow or conform to the shape of a user's upper and/or lower teeth. In some embodiments, the body 102 may be a tray configured in size and shape to fit into the user's mouth and over the upper and/or lower teeth. The body 102 may be made of a rigid, semi-rigid, or flexible material, such as plastics or rubbers. In some embodiments, the body 102 comprises a thermoplastic elastomer (TPE), high-density polyethylene (HDPE), polypropylene (PP), low-density polyethylene (LDPE), polyamides, polyolefin or other resins, polychloro-trifluoroethylene, various thermoplastics, and/or various elastomers. In some embodiments, the body 102 may comprise a food grade polypropylene. The composition of the body 102 is not limited to the above materials, but can be selected for specific characteristics including enough rigidity to provide general support and shape for the oral hygiene device 100a, while also providing enough flexibility to allow the body 102 to fit to the particular anatomy of the user's mouth and teeth. In some embodiments, the oral hygiene device 100a can be provided in a variety of sizes (e.g., small, medium, large, adult, or child) configured for use by users that have different size mouths. In some embodiments, the oral hygiene device 100a can be provided in a size that is generally configured to fit most mouth sizes.

In the illustrated embodiment of FIG. 1A, the body 102 has a generally H-shaped cross-sectional profile 104. The generally H-shaped cross-sectional profile 104 can provide the body 102 with an upper channel 106 and a lower channel 108. The upper channel 106 can be configured to receive of be fitted over the user's upper teeth and the lower channel 108 can be configured to receive or be fitted over the user's lower teeth. For example, during use, the user may insert the oral hygiene device 100a into the mouth such that the upper teeth are positioned within the upper channel 106 and the lower teeth are positioned within the lower channel 108.

One or more of the inside surfaces of the upper channel 106 and the lower channel 108 may include features for cleaning the user's teeth (or otherwise freshening the user's mouth). For example, the inside surfaces of the upper channel 106 and the lower channel 108 can include bristles, foam, rubberized fingers, ribs, textured surfaces, etc., configured to clean the teeth when the oral hygiene device 100a is positioned within the mouth and moved back and forth and/or up and down. The teeth cleaning features are not shown in FIG. 1A, but examples will be shown and described below with reference to other embodiments.

In some embodiments, the teeth cleaning features within the upper channel 106 and the lower channel 108 are formed as part of the body 102. That is, in some embodiments, the teeth cleaning features can be integrally formed with the body 102. For example, the inside surfaces of the upper channel 106 and the lower channel 108 can be configured with a teeth cleaning texture that is molded into the body 102. In some embodiments, the teeth cleaning features can be made from the same material and/or formed at the same time as the body 102. For example, the body 102 and teeth cleaning features can be formed with a one-shot injection molding process in which a single material is injected into a mold to form the body 102 and teeth cleaning features simultaneously.

Advantageously, in some embodiments, the teeth cleaning features may comprise a different material than the body 102. For example, the teeth cleaning features may comprises a softer or more flexible material than the body 102. In such embodiments, the body 102 may be formed from a relatively stiffer or more rigid material in order to provide structural support for the device 100, and the teeth cleaning features can comprise a relatively more compliant or softer material in order to improve user comfort and cleaning efficiency. When made from different materials, the body 102 and the teeth cleaning features can be molded in a two-shot injection or overmolding process. For example, a first injection can be made using a first material to form the body 102, and then a second injection can be made using a second material to form the teeth cleaning features on the body 102.

The teeth cleaning features within the upper channel 106 and/or the lower channel 108 can be attached to the body 102 within the channels 106, 108. In the case of a two-shot injection or overmolding process, the teeth cleaning features are molded (and thereby connected) directly onto the body 102. In other embodiments, the body 102 and teeth cleaning features can be formed separately and then attached to each other, for example, with dental-grade adhesives.

In some embodiments, the upper channel 106 and the lower channel 108 can be lined with bristles, foam, rubberized fingers, ribs, etc., that are attached to the channels 106, 108. The shape, size, and combinations of the teeth cleaning features described herein are not limited to the above materials, but are selected for specific characteristics, including comfort to the mouth and gums and ability to clean teeth.

As illustrated in FIG. 1A, the oral hygiene device 100a includes a handle 110. In the illustrated embodiment, the handle 110 is positioned on a front portion of the body 102. The user can hold the handle while inserting the oral hygiene device 100a into the mouth and use the handle to manipulate the device (e.g., move the device up and down and/or back and forth) to use the device to clean his or her teeth. The handle 110 may be positioned and configured to extend out of the user's mouth between the user's lips when the oral hygiene device 100a is positioned within the mouth.

To use the oral hygiene device 100a, the user may use the handle 110 to insert the oral hygiene device 100a into his or her mouth. The user may position the oral hygiene device 100a such that the user's upper teeth are positioned within the upper channel 106 and the user's lower teeth are positioned within the lower channel 108. In this position, the upper and lower channels 106, 108 may contact the front, bottom, and back surfaces of the user's upper teeth and the front, top, and back surfaces of the user's lower teeth. Further, because of the generally U-shaped body the device 100a can contact all or substantially all of the user's upper and/or lower teeth. As used herein, "contacting substantially all of the user's upper and/or lower teeth" can refer to contact at least 50%, at least 60%, at least 70%, at least 80%, or at least 90% of the user's upper and/or lower teeth.

With the oral hygiene device 100a positioned within the mouth, the handle 110 may extend out of the user's mouth between the user's lips. Using the handle 110, the user may manipulate the oral hygiene device 100a by moving the handle 110 back and forth (e.g., side to side or right and left) and/or up and down. Manipulating the oral hygiene device 100a in this manner causes the teeth cleaning features within the upper channel 106 and the lower channel 108 to clean the teeth. After the user has used the device 100a to clean the teeth, which can be done for an indicated period of time, for example, 10 seconds, 15 seconds, 20 seconds, 30 seconds, 1 minute, 1.5 minutes, or 2 minutes, the user can remove the oral hygiene device 100a from the mouth. In some embodiments, the oral hygiene device 100a is disposable, and can then be discarded.

Notably, in some embodiments, the oral hygiene device 100a can be configured for use without requiring water. As such, the oral hygiene device 100a can be used generally anywhere to quickly clean and/or freshen up the user's mouth, without requiring the user to access a bathroom or running water. To this end, the oral hygiene device 100a can include dabs of mouthwash, breath freshener, toothpaste, desensitizing paste or gel as described below with reference to FIGS. 6A and 6B. In some embodiments, the dabs can be configured for use without requiring additional water. In some embodiments, the oral hygiene device 100a is configured for a single use. For example, the user may use the oral hygiene device 100a one time and then discard the device. In some embodiments, because the U-shaped body 102 covers many, and in some embodiments, all or substantially all of the user's teeth, the oral hygiene device 100a may be able to clean all or substantially all of the user's teeth much quicker than a toothbrush, which generally only contacts a few (e.g., one, two, or three) teeth at a time and must be moved over all the teeth in order to clean the whole mouth.

Figure 1B:
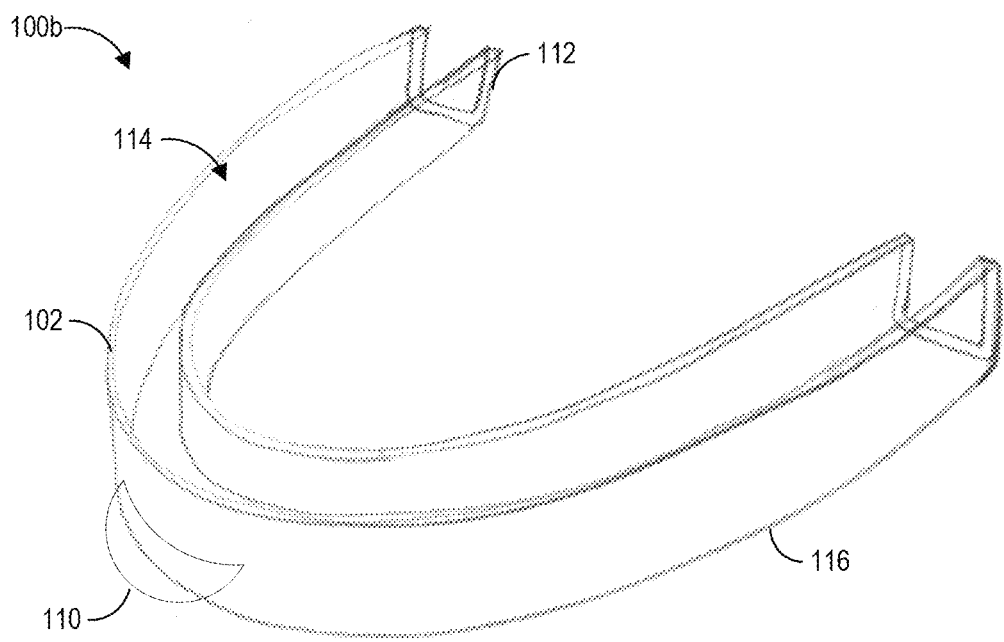
FIG. 1B is a perspective view of an embodiment of an oral hygiene device that includes a U-shaped cross-section.

FIG. 1B is a perspective view of another embodiment of an oral hygiene device 100b. The oral hygiene device 100b is similar in many respects to the oral hygiene device 100a described above with reference to FIG. 1A. However, as shown in FIG. 1B, the oral hygiene device 100b includes a body 102 with a generally U-shaped cross-sectional profile 112 (instead of the H-shaped cross-section 104 of FIG. 1A).

The generally U-shaped cross-sectional profile 112 can provide a single channel 114 in the body 102 of the oral hygiene device 100b (in contrast with the upper and lower channels 106, 108 of the oral hygiene device 100a of FIG. 1A).

Similar to the description above, one or more of the inside surfaces of the channel 114 may include features for cleaning the user's teeth. For example, the inside surfaces of the channel 114 can include bristles, foam, rubberized fingers, ribs, textured surfaces, etc., configured to clean the teeth when the oral hygiene device 100b is positioned within the mouth and moved back and forth and/or up and down. As described above, the teeth cleaning features can be formed as part of the body 102, molded onto the body in a two-shot injection or overmolding process, or attached to the body 102 within the channel 114 and can be made of the same or different materials than the body 102.

With the generally U-shaped cross-sectional profile 114, the oral hygiene device 100b can be configured to clean either the user's upper teeth or the user's lower teeth at a time. In some instances, the device 100b can then be flipped over to clean the other of the user's upper teeth or the user's lower teeth. For example, the user may use insert the oral hygiene device 100b into the mouth such that the channel 114 is oriented in an upward direction and the user's upper teeth can be received within the channel 114. The user may then use the handle 110 to manipulate the device to allow the teeth cleaning features within the channel 114 to clean the user's upper teeth. The user may then remove the oral hygiene device 100b, flip the device over (such that the channel 114 opens in a downward direction), and reinsert the device such that the user's lower teeth are received within the channel 114. The user may again manipulate the device 100b such that the teeth cleaning features clean the user's lower teeth. Alternatively, the user may use the device 100b to clean the lower teeth first, followed by the upper teeth. In some instances, the user may use two of the devices 100b, one to clean the user's upper teeth and one to clean the user's lower teeth. FIGS. 7A-7K, described in more detail below, illustrate a more detailed example of an oral hygiene device 700 that can be used in this manner.

In some embodiments, the oral hygiene device 100b may include teeth cleaning features positioned on a side 116 of the body 102 opposite the channel 114. With reference to the illustrated orientation, the side 116 may be the lower or bottom side of the device. For example, in addition to including teeth cleaning features within the channel 114, the oral hygiene device 100b may also include teeth cleaning features (e.g., bristles, ribs, rubberized figures, foam, etc.) that extend from the lower side 116. Thus, in some embodiments, the oral hygiene device 100b (with its generally U-shaped cross-sectional profile 112) can be configured to clean both the upper and lower teeth of the user at the same time.

Figure 2A:
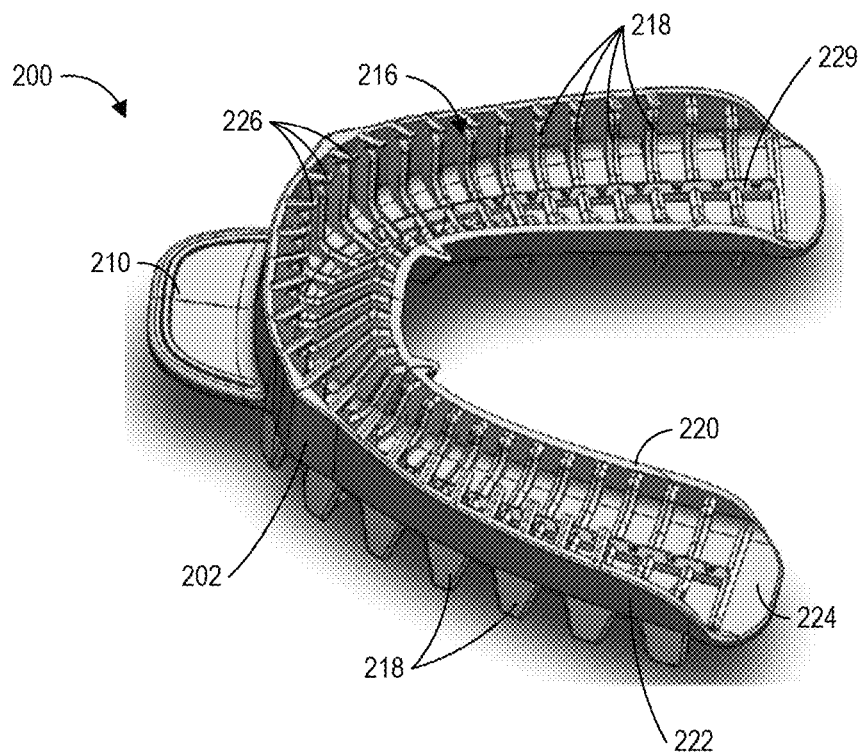
FIG. 2A is a top and side perspective view of an embodiment of an oral hygiene device that includes a plurality of ribs for cleaning top and bottom teeth at substantially the same time.
Figure 2B:
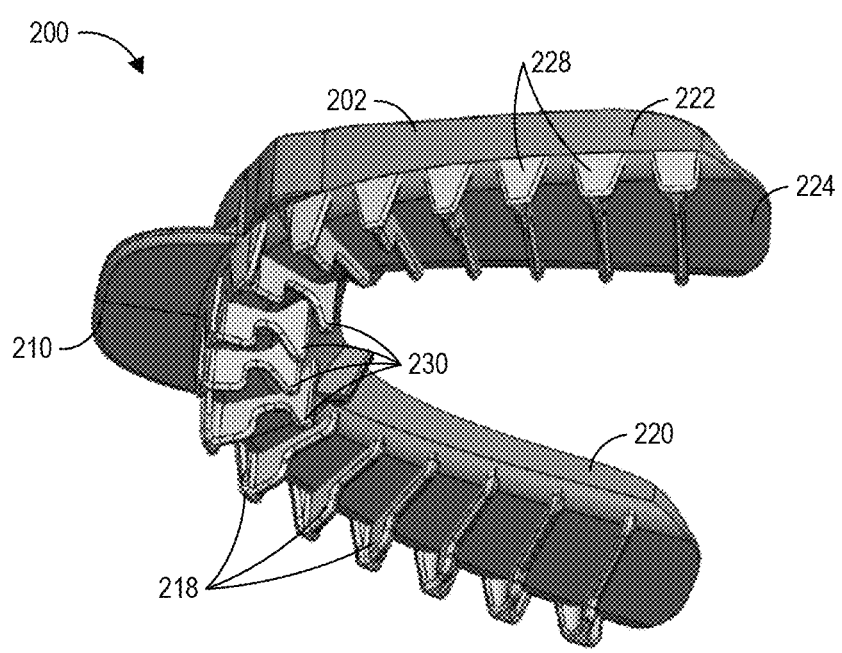
FIG. 2B is a bottom and side perspective view of the oral hygiene device of FIG. 2A.
Figure 2C:
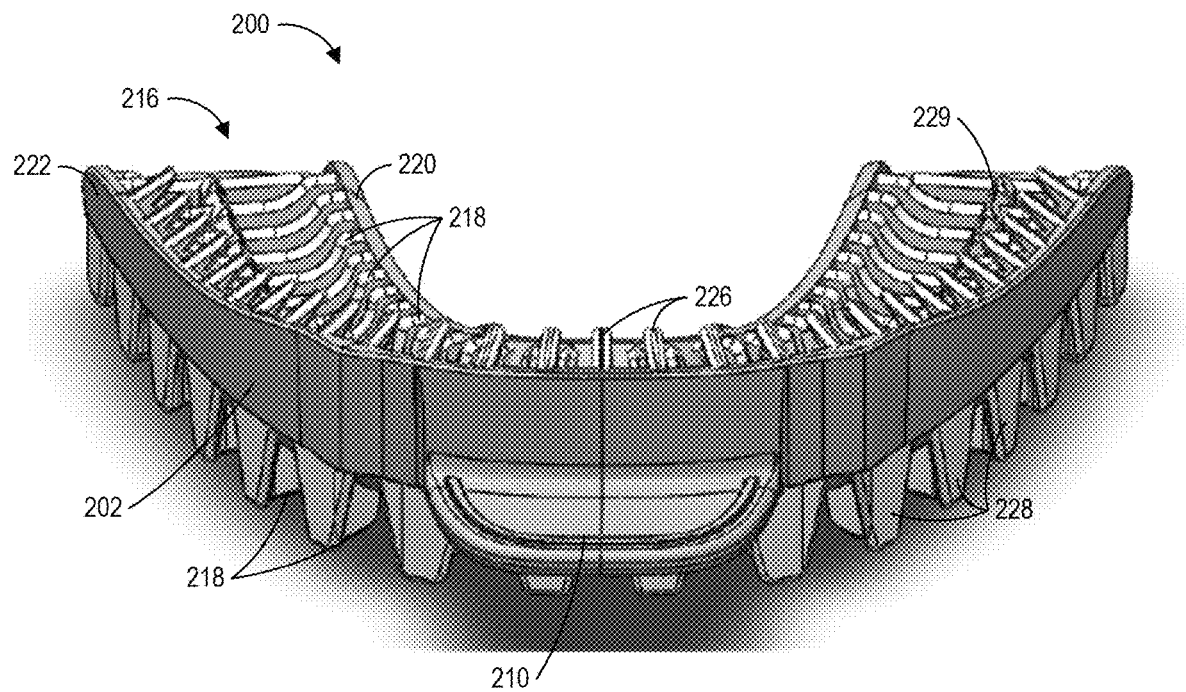
FIG. 2C is a top and front perspective view of the oral hygiene device of FIG. 2A.
Figure 2D:
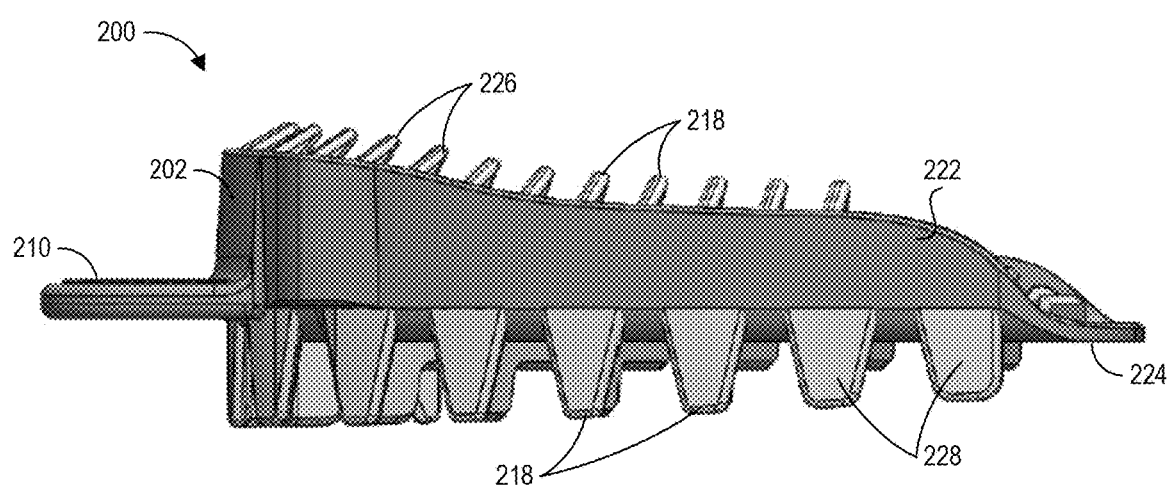
FIG. 2D is a side view of the oral hygiene device of FIG. 2A.
Figure 2E:
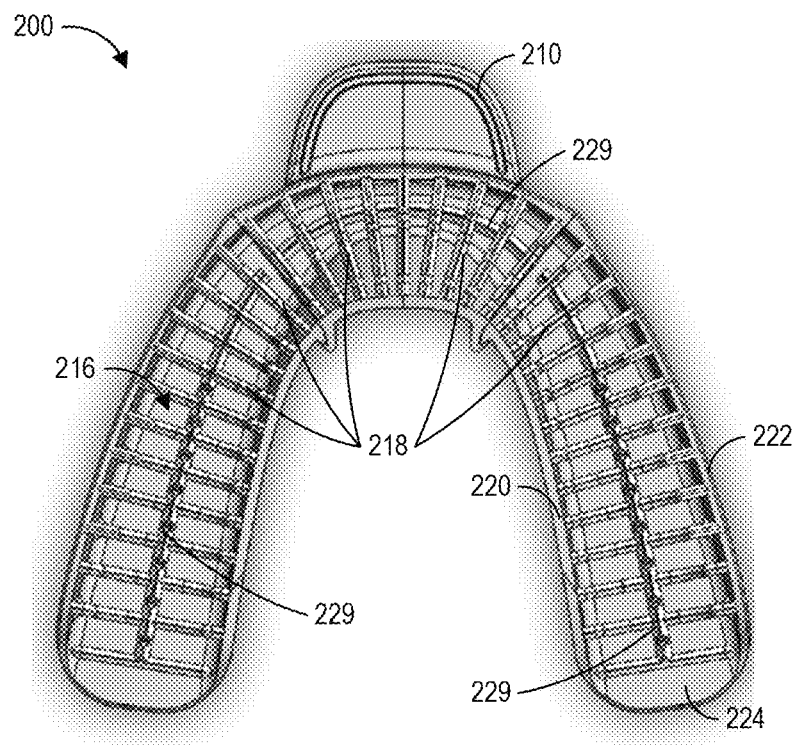
FIG. 2E is a top view of the oral hygiene device of FIG. 2A.
Figure 2F:
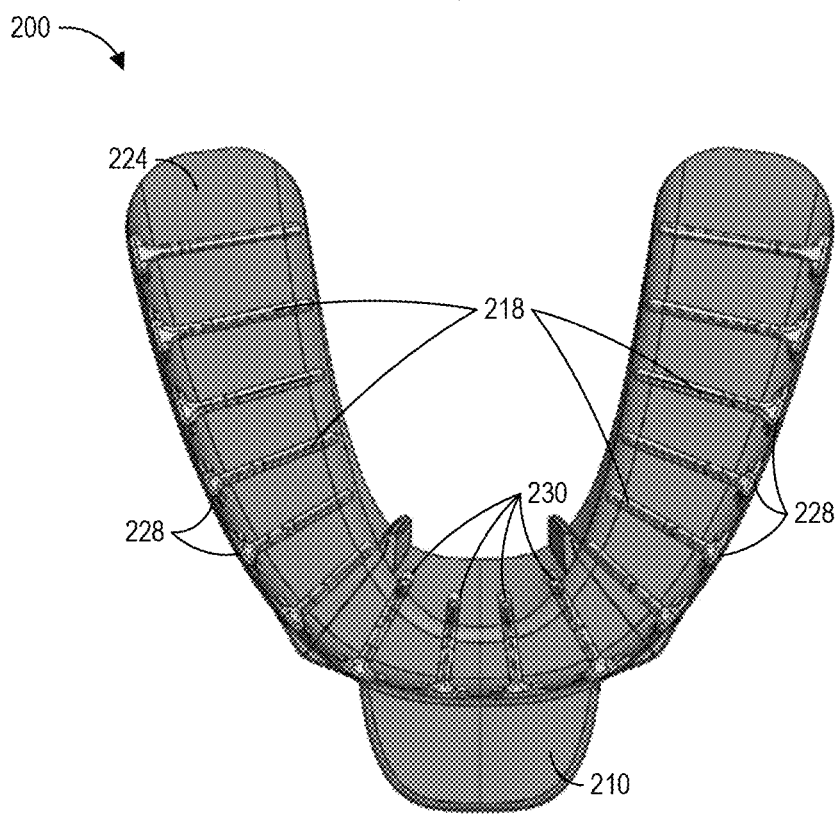
FIG. 2F is a bottom view of the oral hygiene device of FIG. 2A.
Figure 2G:
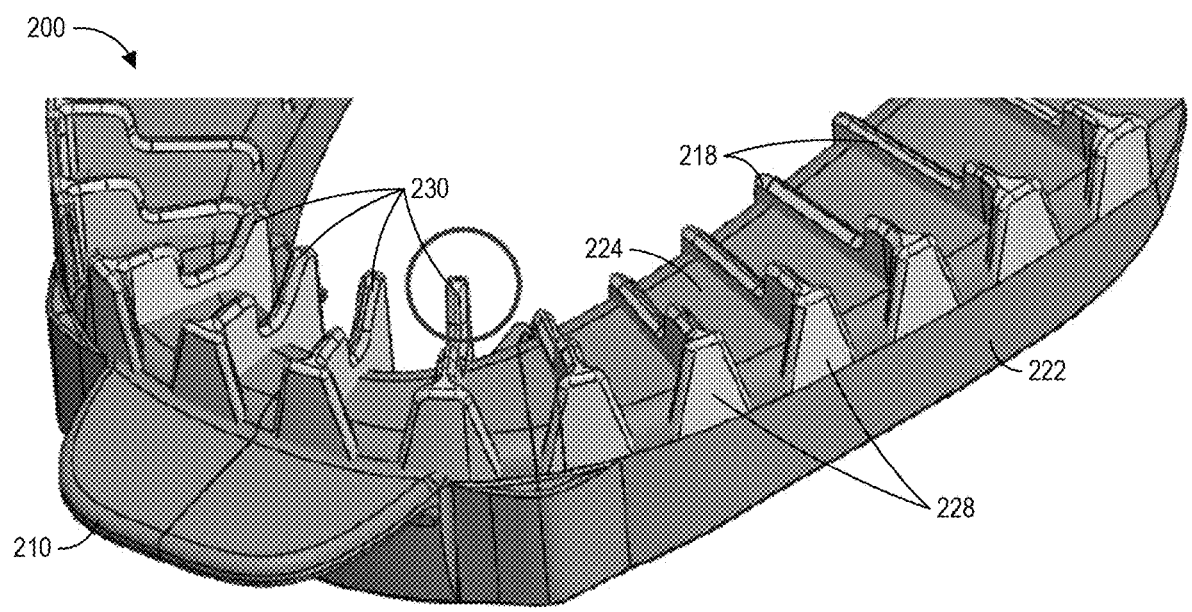
FIG. 2G is a detail view of the oral hygiene device of FIG. 2A, showing an enlarged view of ribs of a bottom side of the oral hygiene device.

FIGS. 2A-2G illustrate views of an embodiment of an oral hygiene device 200 that includes a plurality of ribs 218. The ribs 218 can be the teeth cleaning features described above. The ribs 218 can be positioned on the oral hygiene device 200 for cleaning upper and lower teeth at substantially the same time as shown in the illustrated embodiment. FIG. 2A is a top and side perspective view, FIG. 2B is a bottom and side perspective view, FIG. 2C is a top and front perspective view, FIG. 2D is a side view, FIG. 2E is a top view, FIG. 2F is a bottom view, and FIG. 2G is a detail view of the oral hygiene device 200.

With reference to FIGS. 2A-2G, the oral hygiene device 200 includes a body 202. In the illustrated embodiment, the body 202 is generally U-shaped similar to the oral hygiene devices described previously. For example, the generally U-shaped body 202 can be configured to generally follow the shape of a user's upper and/or lower teeth. As illustrated, the body 202 also includes a generally U-shaped cross-sectional profile, similar to the oral hygiene device 100b described above. The generally U-shaped cross-sectional profile may include an inner wall 220, an outer wall 222, and a bottom wall 224 as shown. The generally U-shaped cross-sectional profile can define a channel 216 within the body 202. The channel 216 can be formed between the inner wall 220 and the outer wall 222 and bounded below by the bottom wall 224. In some embodiments, the body 202 can be configured in size and shape such that the channel 216 is configured to receive the user's upper teeth during use of the oral hygiene device 200. In some embodiments, the body 202 can be configured in size and shape such that the channel 216 is configured to receive the user's lower teeth during use of the oral hygiene device 200.

The body 202 may be made of a rigid, semi-rigid, or flexible material, such as plastic, rubber, a polymer, or other suitable material. In some embodiments, the body 202 is rigid enough to provide general support and shape for the oral hygiene device 200, while remaining flexible enough to allow the body 202 to fit to the particular anatomy of the user's mouth and teeth. In some embodiments, the body 202 comprises a thermoplastic elastomer (TPE), high-density polyethylene (HDPE), polypropylene (PP), low-density polyethylene (LDPE), polyamides, polyolefin or other resins, polychloro-trifluoroethylene, various thermoplastics, and/or various elastomers. In some embodiments, the body 102 may comprise a food grade polypropylene. The composition of the body 202 is not limited to the above materials, but is selected for specific characteristics including enough rigidity to provide general support and shape for the oral hygiene device 200, while including enough flexibility to allow the body 202 to fit to the particular anatomy of the user's mouth and teeth.

The body 202 may be formed such that the walls (e.g., the inner wall 220, the outer wall 222, and the bottom wall 224) are sufficiently thin so as to allow the body 202 to flex and conform to the shape of the user's mouth. For example, in some embodiments, the walls of the body 202 are about 2 mm, 1.5 mm, 1.0 mm, 0.75 mm, 0.5, or 0.25 mm thick. In some embodiments, the nominal thickness of the walls of the body 202 is about 1.2 mm. These thicknesses are provided by way of example, and the thickness of the walls of the body 202 can be selected to provide the desired characteristics described throughout this application.

In some embodiments, the oral hygiene device 200 can be provided in a variety of sizes (e.g., small, medium, large, adult, or child) configured for use by users that have different size mouths. In some embodiments, the oral hygiene device 200 can be provided in a size that is generally configured to fit most mouth sizes.

As illustrated, the oral hygiene device 200 includes a handle 210. The handle 210 can be configured as a tab, although other shapes are possible as described in greater detail below (see, for example, FIGS. 17A-17D). The handle 210 can extend from a front portion of the body 202 so as to be able to extend out of the user's mouth between the user's lips when the oral hygiene device 200 is inserted into the user's mouth. In the illustrated embodiment, the handle 210 extends form the outer wall 222 of the body 202. The handle 210 may be aligned with the bottom wall 224 of the body 202 (as shown), or the handle 210 can be placed in any other desired location. In some embodiments, the oral hygiene device 200 does not include a handle 210 (i.e., the handle 210 may be omitted). Similar to the discussion above, the user may use the handle to manipulate the oral hygiene device 200 to use the oral hygiene device 200 to clean the user's teeth.

Similar to the oral hygiene devices 100a, 100b described generally above, the oral hygiene device 200 can include teeth cleaning features (such as ribs 218) configured to clean the user's teeth when the device is used. In the illustrated embodiment, the teeth cleaning features comprise the ribs 218, although in other embodiments, other types of teeth cleaning features (e.g., foam, bristles, textured surfaces, etc.) can be used in addition to or in place of the ribs 218.

The ribs 218 can be formed of the same material as the body 202, or the ribs 218 can be formed of a softer or more flexible material than the body 202 as described above. Advantageously, forming the body 202 and the ribs 218 of different materials may improve functionality, comfort, and efficiency of the device. For example, as described above the body 202 can be formed of a generally stiffer and more rigid material to provide structural support for the device 200, while the ribs 218 can be formed of a generally less rigid or softer material. The softer material of the ribs 218 can provide more user comfort during use, while also better conforming to the user's mouth and teeth shape to provide increased cleaning efficiency.

The ribs 218 can be integrally formed with the body 202 or can be separately formed and attached to the body 202. In some embodiments, the body 202 and ribs 218 are co-molded in a two-step molding process, such as a double shot or overmolding process, as described above. In other embodiments, the body 202 and the ribs 218 can be formed separately and then attached to one another. In some embodiments, the ribs 218 comprise a thermoplastic elastomer (TPE), silicon rubber, high-density polyethylene (HDPE), polypropylene (PP), low-density polyethylene (LDPE), polyamides, polychlorotrifluoroethylene, various thermoplastics, and/or various elastomers. In some embodiments, the ribs 218 comprise a food grade TPE or thermoplastic polyurethane (TPU). The composition of the ribs 218 is not limited to the above materials, but can be selected for specific characteristics including the ability to clean on and around teeth. In some embodiments, the ribs 218 may comprise a material with a Shore A hardness of between 70 and 100, between 75 and 95, or between 80 and 90, or between 85 and 90. Shore A hardnesses within these ranges can provide the comfort and efficiency advantages discussed above.

In the illustrated embodiment, the oral hygiene device 200 includes ribs 218 positioned both in the channel 216 and extending from the bottom wall 224 of the body 202 so that the ribs 218 can contact the user's upper and lower teeth at the same time. Such an embodiment can advantageously reduce the total time required to freshen the mouth or clean the teeth be cleaning both the top and bottom teeth simultaneously. In some embodiments, the oral hygiene device 200 may include ribs 218 on only one side of the body 202 (e.g., the upper side or the lower side).

In some embodiments, the shape of the ribs 218 can be formed in order to contour to a user's mouth and teeth. In some embodiments, the ribs 218 are about 1.2 mm, 1.0 mm, 0.8 mm, 0.6 mm, or 0.5 mm thick, although other thicknesses, both thinner and thicker than these example values are possible. The thickness can be selected to facilitate teeth cleaning efficiency.

In some embodiments, the size and shape of the ribs 218 varies depending upon the location of the ribs 218 on the body 202. For example, the size and shape of the ribs 218 can be adjusted to suit the general size and shape of the particular teeth the ribs 218 will generally overlie when the oral hygiene device 200 is positioned within the mouth. Ribs 218 that are positioned on the body 202 to generally overlie molars (which are generally thicker) may have a different shape than ribs 218 that are positioned to overlie incisors (which are generally thinner). The ribs 218 can also be configured such that they contact more than one surface of the user's teeth at a time. For example, the ribs 218 can be configured to contact the front, bottom and back surfaces of the user's upper teeth and/or the front, top, and back surfaces of the user's teeth simultaneously.

The ribs 218 may also have a shape that is adapted to clean the user's gums and/or gum line. For example, the ribs 218 may be angled with respect to the gums so as to clean the space between the gums and the teeth. In some examples, the ribs 218 are configured to contact the gums at an angle between 30 and 60 degrees, between 40 and 50 degrees, or approximately 45 degrees, as discussed below with reference to the fingers 226 of the ridges.

In the illustrated embodiment, the oral hygiene device 200 includes ribs 218 positioned within the channel 216. The ribs 218 positioned within the channel 216 can be configured to clean the upper teeth of the user. As illustrated, ribs 218 extend generally across the channel 216 from the inner wall 220 to the outer wall 222, as well as along the inner surfaces of the inner wall 220 and the outer wall 222. Such a configuration can allow the ribs to contact multiple surfaces of the user's teeth simultaneously as described above.

In the illustrated embodiment, the oral hygiene device 200 includes about 33 ribs in the channel 216, although other numbers are possible (e.g., about 15, about 20, about 25, about 30, about 35, about 40, about 45, or about 50 ribs 218). The ribs 218 may be spaced evenly or unevenly. In some embodiments, the ribs 218 are spaced apart so as to be aligned with the spaces between the user's teeth or the interproximal contact area (IPC) when the oral hygiene device 200 is inserted into the mouth. In some embodiments, there can be more ribs 218 disposed in the channel 216 than there are upper teeth. This can provide additional coverage for teeth cleaning and can reduce the amount a user would need to move the oral hygiene device 200 in order to contact and adequately clean all the teeth. In some embodiments, the ribs 218 are spaced about 2 mm, 4 mm, 6 mm, 8 mm, or 10 mm apart, although other spacings are possible. The position and spacing of the ribs 218 can be selected to facilitate operation of the device. For example, the ribs 218 can be positioned so as to efficiently clean the teeth. In some embodiments, the oral hygiene device 200 can have different sizes to accommodate different mouth sizes. For example, in some embodiments, the oral hygiene device 200 can be adapted for use in a child's mouth. In this case, the oral hygiene device 200 can include fewer ribs 218 and/or different rib spacing, based on a child's mouth's dimensions and/or number of teeth. In some embodiments, the oral hygiene device 200 can be adapted for use in an adult's mouth. In some embodiments, the spacing of the ribs 218 is a function of the average dimensions of each tooth.

In some embodiments, the shape of the individual ribs 218 may be varied to suit the particular teeth the ribs will contact during use. For example, as illustrated, the ribs 218 positioned within the back parts of the channel 216 (i.e., the ribs configured to clean molars) can have a wider cutout shape configured to match the thickness of the molars, and the ribs 218 positioned within the front part of the channel 216 (i.e., the ribs configured to contact incisors) have a narrower cutout shape configured to match the thickness of the incisors). In some embodiments, the shape of the ribs 218 positioned within the channel 216 is configured to contact the front surface, bottom surface, and back surface of the user's upper teeth As shown in FIGS. 2A, 2C, and 2D, one or more of the ribs 218 positioned within the channel 216 may include a finger 226. The finger 226 be configured as a protrusion or extension that extends from the ribs 218. In some embodiments, the finger 226 can be configured to clean the gum line. In some embodiments, the finger 226 is angled at an angle of between 30 and 60 degrees, between 40 and 50 degrees, or approximately 45 degrees with respect to the bottom wall 224, although other angles are also possible. The angle of the fingers 226 can be set in order to provide an optimal cleaning angle when the finger 226 contacts the teeth and/or the gum line. In some embodiments, the cleaning angle varies depending upon the location within the mouth. For example, the angle at the front teeth may differ from the angle at the back teeth. In some embodiments, fingers 226 can also be included to clean the inner gum line and/or to clean the inner or outer gum line on the upper and/or lower teeth. The bass technique is a common conventional toothbrush technique for preventing and controlling gum disease by brushing around and under the gum line where bacteria and plaque tend to accumulate. Using the bass technique, a user places the toothbrush parallel to his or her teeth with the bristles toward the gums and then tilts the brush to a 45 degree angle to position the bristles slightly under the gum line. The fingers 226 of the ribs 216 can be configured at a 45 degree angle so as to provide similar benefits as the bass technique. The fingers 226 can, for example, be configured to clean the gum line.

The ribs 218 positioned within the channel 216 may be connected by a spline 229 as shown. The spline 229 can be configured to clean the occlusal surface of the teeth. The spline 229 can be positioned within the channel 216 on the bottom wall 224. In some embodiments, the spline 229 runs continuously from one end of the channel 216 to the other. The shape, size, materials, and placement of the spline 229 can be based on specific desirable characteristics, such as the ability to clean the occlusal surface of each tooth. In some embodiments, the spline 229 is broken at various points along its length to comprise various discrete sections. For example, as best seen in FIG. 2E, the spline 229 can include at least three sections as shown. These three sections may facilitate a dual-hinged design, as shown, for example, in FIGS. 3A-4B, described below.

Opposite the channel 216, the oral hygiene device 200 also includes ribs 218 extending outwardly (e.g., downwardly) from the bottom wall 224. These ribs 218 can be configured to clean the user's bottom teeth. As illustrated, the ribs 218 extend generally across the bottom wall 224 form the inner wall 220 to the outer wall 222, although this need not be the case in all embodiments. In the illustrated embodiment, the oral hygiene device 200 includes 16 ribs extending from the bottom wall 224 opposite the channel 216, although other numbers are possible (e.g., about 10, about 20, about 25, about 30). As with the ribs 218 positioned within the channel 216, the ribs 218 positioned opposite the channel 216 may be spaced evenly or unevenly. The spacing or number of the ribs 218 positioned within the channel 216 need not match the spacing or number of the lower ribs 218 positioned opposite the channel 216. In some embodiments, the spacing of the lower ribs 218 is greater than the spacing of the upper ribs 218 (for example, as shown). In some embodiments, the number of lower ribs 218 is less than the number of upper ribs 218. In some embodiments, the ribs 218 positioned opposite the channel are about 2 mm, 4 mm, 6 mm, 8 mm, 10 mm, 12 mm, 14 mm, 16 mm, 18 mm, or 20 mm apart, although other spacings are possible.

As noted previously, the shape of the individual ribs 218 may be varied to suit the particular teeth the ribs 218 will generally overlie during use. This may also be true for the lower ribs 218. For example, the ribs 218 positioned within the back parts of device 200 (i.e., the ribs configured to overlie the lower molars) can include a wider cutout shape configured to match the thickness of the molars, and the ribs 218 positioned on the front part of the device 200 (i.e., the ribs configured to overlie the front incisors) can include a narrower cutout shape configured to match the thickness of the incisors). In some embodiments, the shape of the lower ribs 218 extending from the bottom wall 224 are configured to contact the front surface, top surface, and back surface of the user's lower teeth.

As best seen in FIGS. 2B, 2F, and 2G, the lower ribs 218 may comprise a general T-shape, each having a flange 228 that extends generally aligned with and parallel to the outer wall 222. In some embodiments, the flange 228 provides structural support for the lower ribs 218. In some embodiments, the flange 228 may not contact the teeth during use. The size of the flange 228 can be reduced from the size illustrated in the figures.

As shown in FIGS. 2B and 2G, the front most lower ribs 218 can include an angled finger 230 formed on the inner most side of the ribs 218. The finger 230 may be configured to clean the back side of the lower front teeth and/or the gum line along the back of the lower front teeth. In the illustrated embodiment, the four front-most lower ribs 218 include fingers 230. In other embodiments, other numbers of the lower ribs 218 can include the finger 230 (for example, one, two, three, four, five, six, or more of the lower ribs 218 can include the finger 230). Others of the lower ribs 218 (for example, the ribs 218 configured to be positioned over lower molars) can include an increased height on the outer edge of the ribs 218 and a decreased height on the inner edge of the ribs 218.

Figure 3A:
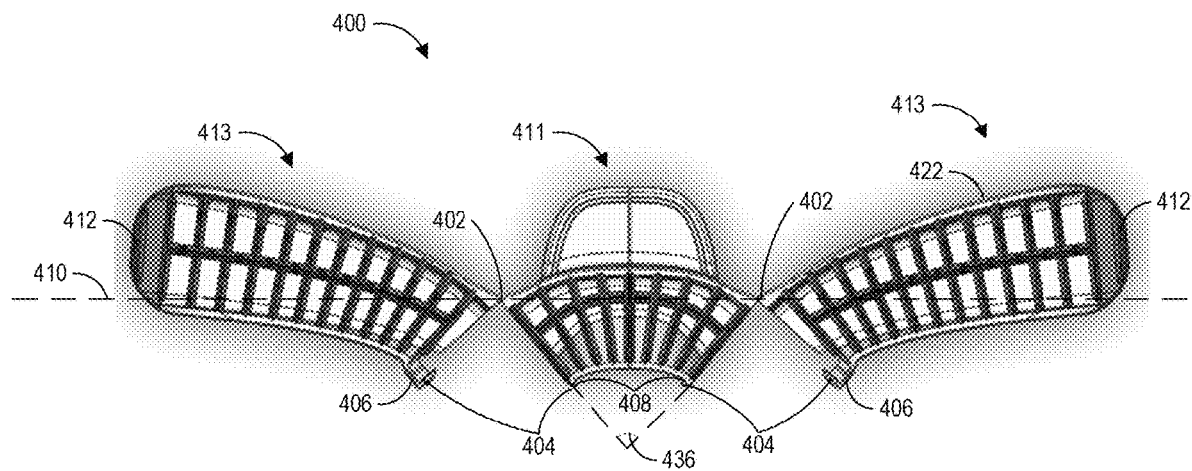
FIG. 3A is a top view of an embodiment of an oral hygiene device that includes dual hinges with the device shown in an open configuration.
Figure 3B:
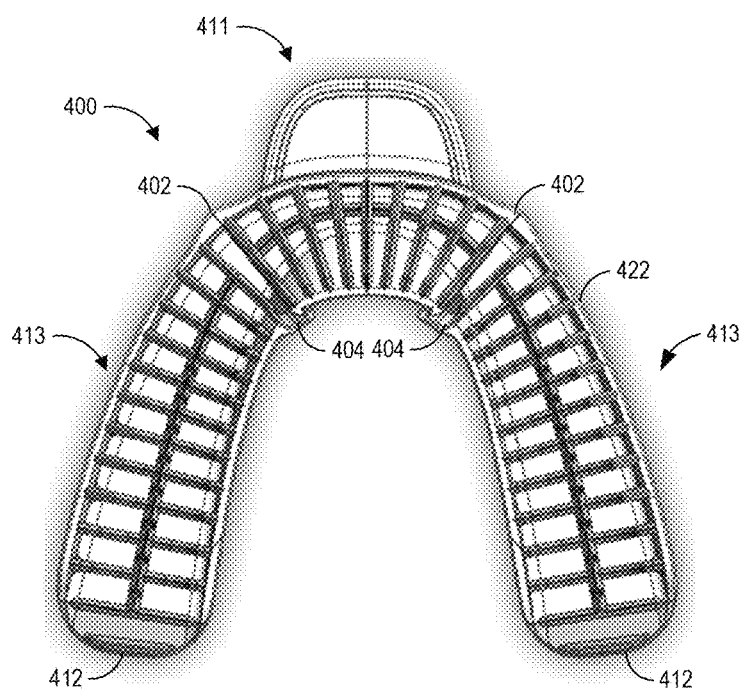
FIG. 3B is a top view of the oral hygiene device of FIG. 3A that illustrates the device in a closed configuration.

FIGS. 3A and 3B are top views of an embodiment of an oral hygiene device 400 that includes dual hinges 402. The dual hinges 402 allow the oral hygiene device 400 to transition between an open configuration (as shown in FIG. 3A) and a closed configuration (as shown in FIG. 3B). As shown in FIG. 3A, in the open configuration, the dual hinges 402 allow the device to transition from a U-shape (for example, as shown in FIGS. 1A-1B and 2A-2G) to a more linear shape that extends generally along an axis 410. This may be advantageous as it may allow the oral hygiene device 400 to be packaged in longer and thinner packages (see FIGS. 5A-5C described below) which may be more space efficient and easier to carry. As shown in FIG. 3B, in the closed configuration, the dual hinges 402 allow the oral hygiene device 400 to transition to a U-shape configured to match the shape of the user's mouth and teeth.

In the illustrated embodiment, the body of the oral hygiene device 400 is divided into three sections: a front section 411, and two rear sections 413. The sections can be formed by manufacturing or cutting the body of the oral hygiene device 400 with an angle 436 as shown in FIG. 3A. In some embodiments, the body is molded as a single piece (e.g., with a single shot or double shot injection molding process as described above), which includes the three sections in an open configuration as shown in FIG. 3A. In some embodiments, the angle 436 is between 60 and 140 degrees.

In one embodiment, the angle 436 is about 80 degrees. In another embodiment, the angle is about 120 degrees. One of skill in the art will appreciate that the angle 436 may be varied to control the overall thickness of the product in the open configuration. For example, an angle 436 of about 120 degrees may allow the device 400 to fit into a thinner container in the open configuration than an angle of about 80 degrees.

In the illustrated embodiment, the oral hygiene device 400 includes two hinges 402. The hinges 402 connect each rear section 413 to one side of the front section 411. The hinges 402 may be positioned on the outer wall 422 of the oral hygiene device 400. In some embodiments, the hinges 402 are living hinges. In some embodiments, the hinges 402 are mechanical hinges. The hinges 402 can be integrally molded with the body 402.

Opposite the hinges 402, the oral hygiene device 400 may include locking mechanisms 404. The locking mechanisms 404 can be integrally molded with the body. The locking mechanisms 404, can be configured to secure the shape of the oral hygiene device 400 in the closed configuration. Various types of locking mechanisms are possible. For example, as illustrated, each locking mechanism comprises a latching member 406 and a catching member 408. To secure the locking mechanism 404, the latching member 406 engages with the catching member 408. Other types of locking mechanisms 404 are possible. The locking mechanism 404 can be selected for specific characteristics including ease of use, efficiency of locking, and small size.

Figure 4A:
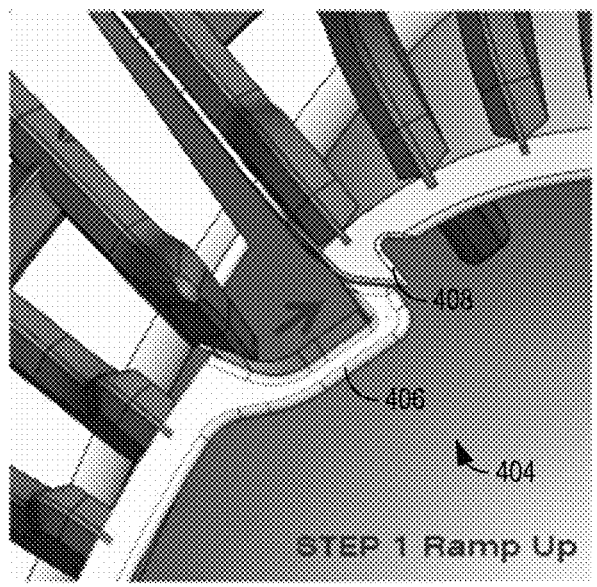
FIG. 4A is a detail view of an embodiment of a locking mechanism for the oral hygiene device of FIG. 3A illustrated just prior to locking into place.
Figure 4B:
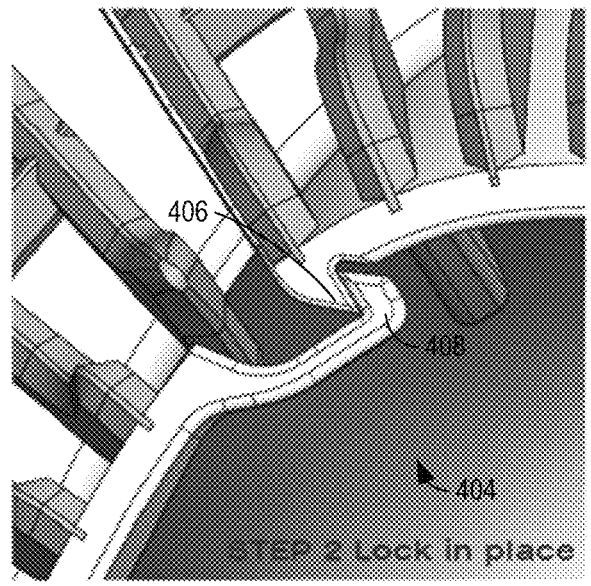
FIG. 4B is a detail view of the locking mechanism of FIG. 4A illustrated locked into place.

FIGS. 4A and 4B are detail views of an embodiment of the locking mechanism 404. FIG. 4A illustrates the locking mechanism 404 just prior to locking into place, and FIG. 4B illustrates the locking mechanism 404 locked into place. As shown in FIG. 4A, prior to locking, the latching member 406 can contact (without lockingly engaging) the catching member 408. To lockingly engage, the locking member 406 must deflect outwardly to allow a hooked end of the locking member 406 to pass the catching member 408. Once the hooked end passes the catching member 408 it falls back behind it, locking the locking mechanism 404 in place.

In some embodiments, the user can release the locking mechanisms 404 to return the oral hygiene device 400 to the open configuration. In some embodiments, once locked, the locking mechanisms 404 remain locked (i.e., one time use).

Returning to FIGS. 3A and 3B, in some embodiments, the rear most portions 412 of the oral hygiene device 400 can be made from a soft material to improve the comfort of the device. For example, in some embodiments, the rearmost portions 412 of the bottom wall (and/or side walls) are made of the same material as the ribs, rather than the same material as the body. As the user manipulates the device to clean the teeth, the rearmost portions 412 may contact the user's mouth and using a softer material in these areas may improve the experience.

The features illustrated with respect to FIGS. 3A-4B can be included on any of the other oral hygiene devices described herein. For example, the oral hygiene device 700 of FIGS. 7A-7K can include a hinged design similar to the oral hygiene device 400.

Figure 5A:
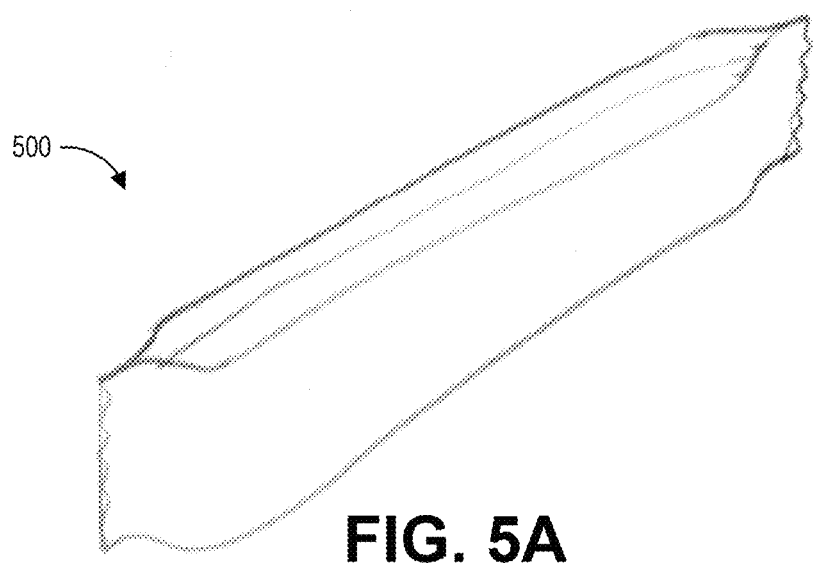
FIG. 5A is a perspective view of an embodiment of a container for an oral hygiene device.
Figure 5B:
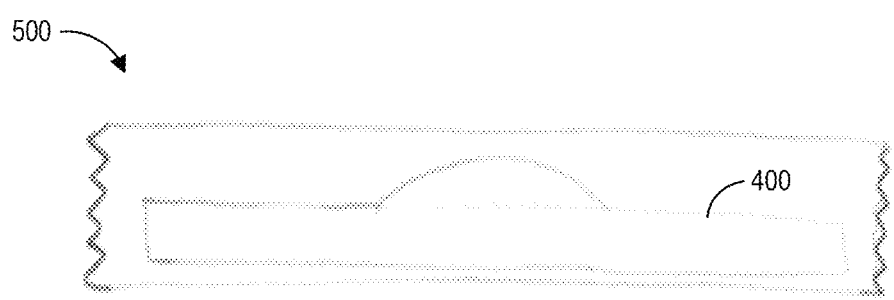
FIG. 5B is a front view of the container of FIG. 5A and illustrates how the oral hygiene device may fit within the container.
Figure 5C:
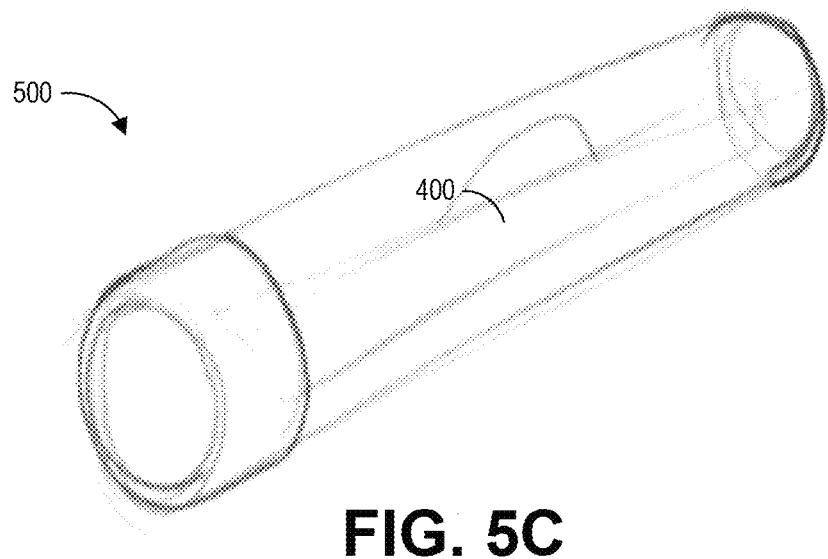
FIG. 5C is a perspective view of another embodiment of a container for an oral hygiene device.

FIGS. 5A-5C show example containers or packages 500 for oral hygiene devices. FIG. 5A is a perspective view of an embodiment of a container 500 for an oral hygiene device. In this embodiment, the container 500 comprises an elongated wrapper, similar to a candy wrapper. The container 500 can be configured to enclose an oral hygiene device that is in an open, elongated configuration, for example as shown in FIG. 3A. FIG. 5B is a front view of the container 500 of FIG. 5A and illustrates how the oral hygiene device 400 of FIGS. 3A-4B may fit within the container 500, for example.

FIG. 5C is a perspective view of another embodiment of a container 500 for an oral hygiene device. In this embodiment, the container 500 comprises an elongated tube. The elongated tube may include a cap. Again, similar to the container shown in FIGS. 5A-5B, the container 500 of FIG. 5C can be configured to enclose an oral hygiene device 400 that is in an open, elongated configuration, for example as shown in FIG. 3A. The materials of the containers or packages are selected for specific characteristics, including ability to withstand friction and force, such as in a purse, briefcase, or suitcase.

In other embodiments, various containers can be provided that are configured to enclose oral hygiene devices in their closed or U-shaped configurations.

As mentioned previously, in some embodiments, the oral hygiene devices described herein are configured to be portable and/or disposable. Those of ordinary skill in the art, upon consideration of this disclosure, will appreciate that the size, shape, and type of container selected to facilitate carrying the oral hygiene device in a space efficient manner suitable for a pocket or bag.

Figure 6A:
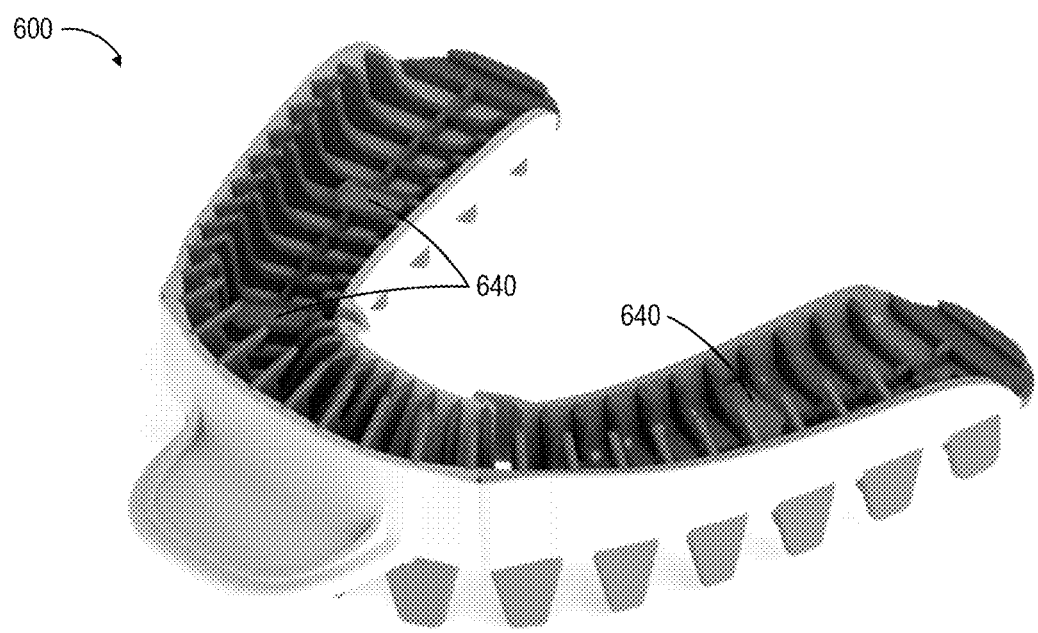
FIG. 6A is a top perspective view of an embodiment of an oral hygiene device that includes beads of mouthwash, breath freshener, toothpaste, desensitizing paste or gel, or whitening paste or gel.
Figure 6B:
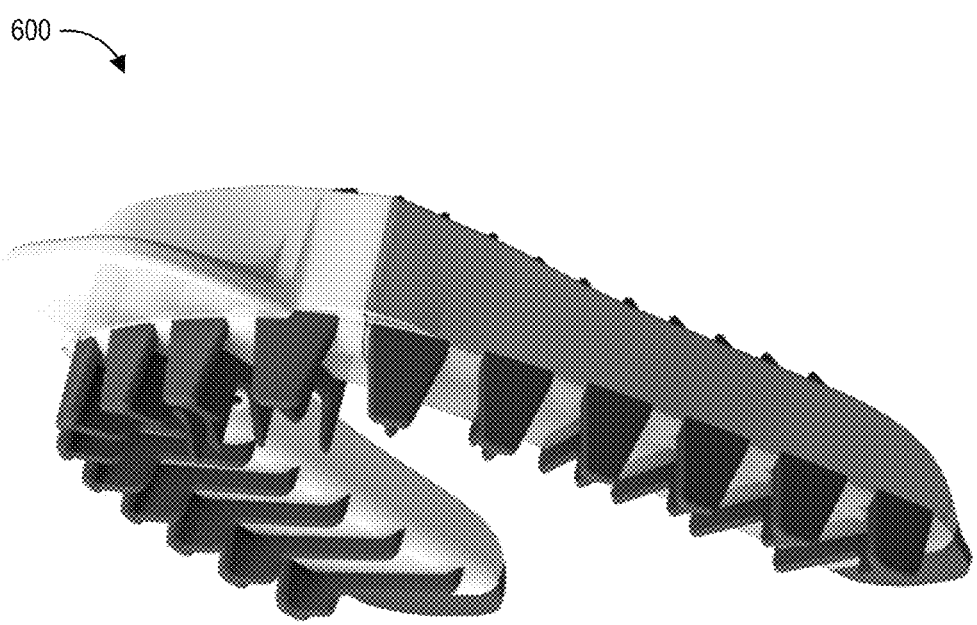
FIG. 6B is a bottom perspective view of the oral hygiene device of FIG. 6A.
Figure 6C:
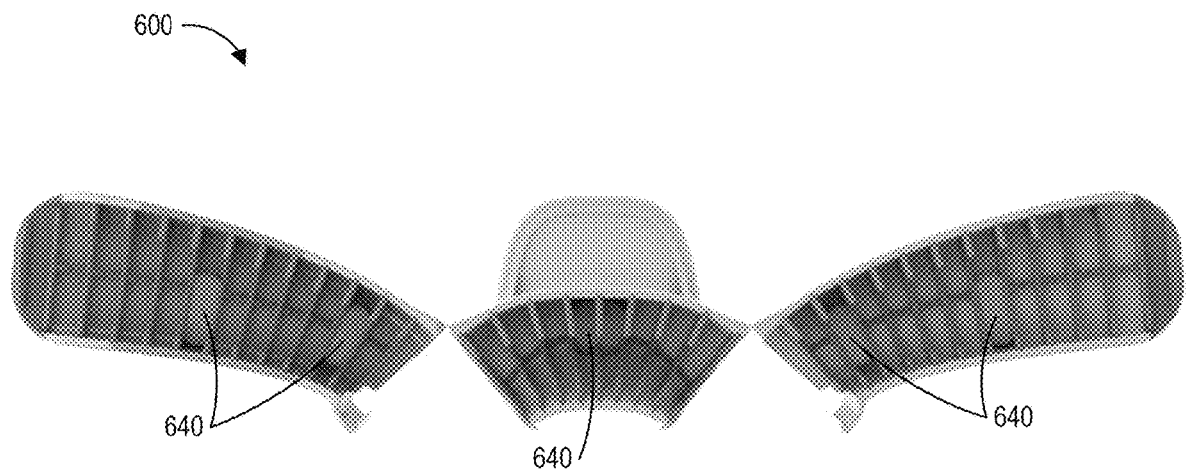
FIG. 6C is a top view of the oral hygiene device of FIG. 6A in an open configuration.
Figure 6D:
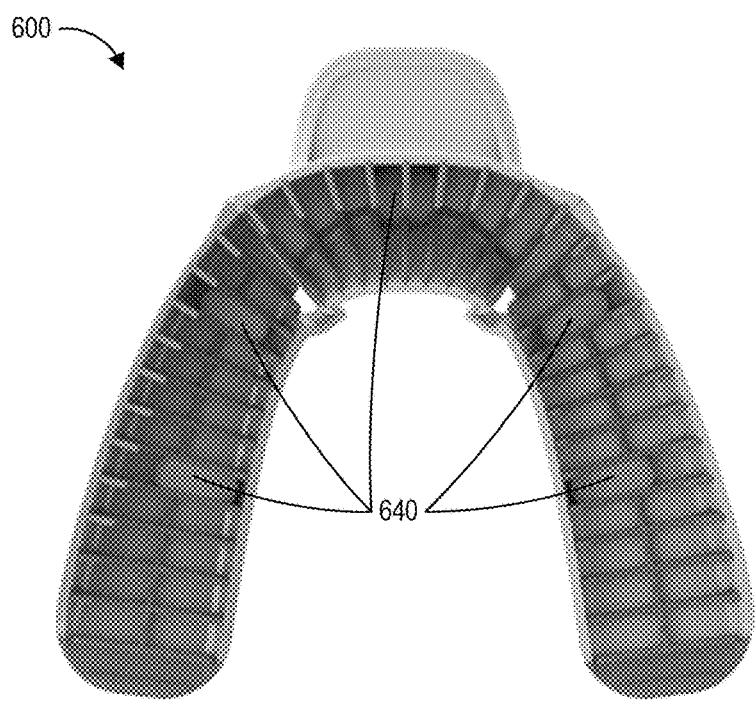
FIG. 6D is a top view of the oral hygiene device of FIG. 6A in a closed configuration.

FIGS. 6A-6D illustrate views of an embodiment of an oral hygiene device 600 that includes beads 640 of mouthwash, breath freshener, toothpaste, desensitizing paste or gel, or whitening paste or gel. FIG. 6A is a top perspective view and FIG. 6B is a bottom perspective view. In the illustrated embodiment, the oral hygiene device 600 also includes the hinged design described above. FIG. 6C illustrates the oral hygiene device 600 in an open configuration, and FIG. 6D illustrates the device in a closed configuration.

In the illustrated embodiment, five beads 640 of mouthwash, breath freshener, toothpaste, desensitizing paste or gel, or whitening paste or gel are shown, but other numbers of beads 640, as well as other positions for the beads 640, are possible. In some embodiments, the beads 640 comprise are referred to as "dabs." As mentioned previously, in some embodiments, the oral hygiene devices described herein are configured to be useable without water or toothpaste, as such the beads 640 of mouthwash, breath freshener, toothpaste, desensitizing paste or gel, or whitening paste or gel can be configured to also be useable without requiring water and/or without requiring the user to rinse out his or her mouth after use. Alternatively, in some embodiments, the beads 640 can comprise beads of a dentifrice that can be used with water during use of the device. The size, shape, materials, and location of the beads is selected for specific characteristics including the ability to freshen breath or clean the mouth.

In some embodiments, the beads 640 are positioned within pockets or indentations formed on the device 600. For example, as best seen in FIGS. 6C and 6D, the beads 640 can be positioned within pockets that are formed of the same material as the ribs of the device 600. These pockets can be formed with the device 600 as the device is molded. The beads 640 can then be applied to the pockets later during manufacturing. Alternatively, the pockets can be formed as part of the body of the device.

In the illustrated embodiment of FIGS. 6A-6D, the beads 640 are positioned on the upper portion of the device. In some embodiments, no beads 640 are positioned on the lower power of the device. In some embodiments, beads 640 are positioned on both the upper and lower portions of the device. In some embodiments, an upper portion of the device may include a different number of beads 640 than a lower portion of the device.

In some embodiments, the beads 640 of mouthwash, breath freshener, toothpaste, desensitizing paste or gel, or whitening paste or gel are positioned on the oral hygiene device so as to be automatically activated when the oral hygiene device is used by the user. In some embodiments, the beads 640 are activated by biting, grinding, or crushing by the user's teeth during use of the oral hygiene device 600. In some embodiments, the beads 640 dissolve into the mouth during use.

In some embodiments, the beads or dabs 640 can comprise a formulation configured to clean and freshen one's mouth, and that can be used without water. In some embodiments, the beads or dabs 640 comprise a formulation that is safe to be swallowed. This can allow a user to quickly and easily use the oral hygiene devices anywhere. In other embodiments, the beads or dabs 640 can comprise formulations that are not safe to be swallowed (such as formulations that include fluoride or mouthwash). Several example formulations are shown in the following tables.

Sample Formulation 1

| Ingredient | % w/w | g/batch | Function |
|---|---|---|---|
| Xanthan Gum | 0.500 | 0.500 | Viscosity Builder |
| Poloxamer P407 | 30.000 | 30.000 | Gelling Agent |
| Glycerin | 10.000 | 10.000 | Humectant |
| Xylitol | 10.000 | 10.000 | sweetener |
| SLS | 1.500 | 1.500 | Foaming |
| FD&C Blue 2 | 0.050 | 0.050 | Color |
| Mint | 2.000 | 2.000 | Flavor |
| Water | 45.950 | 45.950 | Solvent |

Sample Formulation 2

| Ingredient | % w/w | g/batch | Function |
|---|---|---|---|
| Xanthan Gum | 0.500 | 0.500 | Viscosity Builder |
| Poloxamer P407 | 25.000 | 25.000 | Gelling Agent |
| Glycerin | 10.000 | 10.000 | Humectant |
| Xylitol | 10.000 | 10.000 | sweetener |
| SLS | 1.500 | 1.500 | Foaming |
| FD&C Blue 2 | 0.050 | 0.050 | Color |
| Mint | 1.000 | 1.000 | Flavor |
| Water | 51.950 | 51.950 | Solvent |

Sample Formulation 3

| Ingredient | % w/w | g/batch | Function |
|---|---|---|---|
| Xanthan Gum | 0.500 | 0.500 | Viscosity Builder |
| Poloxamer P407 | 25.000 | 25.000 | Gelling Agent |
| Glycerin | 10.000 | 10.000 | Humectant |
| Sucralose | 0.125 | 0.125 | sweetener |
| SLS | 1.500 | 1.500 | Foaming |
| FD&C Blue 2 | 0.050 | 0.050 | Color |
| Mint | 1.500 | 1.500 | Flavor |
| Water | 61.325 | 61.325 | Solvent |

Sample Formulation 4

| Ingredient | % w/w | g/batch | Function |
|---|---|---|---|
| Xanthan Gum | 0.750 | 0.750 | Viscosity Builder |
| Poloxamer P407 | 20.000 | 20.000 | Gelling Agent |
| Glycerin | 10.000 | 10.000 | Humectant |
| Sucralose | 0.125 | 0.125 | sweetener |
| SLS | 1.000 | 1.000 | Foaming |
| FD&C Blue 2 | 0.050 | 0.050 | Color |
| Mint | 1.500 | 1.500 | Flavor |
| Water | 66.575 | 66.575 | Solvent |

Sample Formulation 5

| Ingredient | % w/w | g/batch | Function |
|---|---|---|---|
| Xanthan Gum | 1.000 | 1.000 | Viscosity Builder |
| Poloxamer P407 | 15.000 | 15.000 | Gelling Agent |
| Glycerin | 10.000 | 10.000 | Humectant |
| Sucralose | 0.125 | 0.125 | sweetener |
| SLS | 1.000 | 1.000 | Foaming |
| FD&C Blue 2 | 0.050 | 0.050 | Color |
| Mint | 1.500 | 1.500 | Flavor |
| Water | 71.325 | 71.325 | Solvent |

Sample Formulation 6

| Ingredient | % w/w | g/batch | Function |
|---|---|---|---|
| Xanthan Gum | 1.000 | 1.000 | Viscosity Builder |
| Poloxamer P407 | 18.000 | 18.000 | Gelling Agent |
| Glycerin | 10.000 | 10.000 | Humectant |
| Sucralose | 0.125 | 0.125 | sweetener |
| SLS | 0.500 | 0.500 | Foaming |
| FD&C Blue 2 | 0.050 | 0.050 | Color |
| Mint | 1.500 | 1.500 | Flavor |
| Water | 68.825 | 68.825 | Solvent |

Sample Formulation 7

| Ingredient | % w/w | g/batch | Function |
|---|---|---|---|
| Xanthan Gum | 1.000 | 1.000 | Viscosity Builder |
| Poloxamer P407 | 18.000 | 18.000 | Gelling Agent |
| Glycerin | 10.000 | 10.000 | Humectant |
| Sucralose | 0.125 | 0.125 | sweetener |
| SLS | 0.500 | 0.500 | Foaming |
| Green DB-110004 | 0.005 | 0.005 | Color - Dye Blend |
| Mint | 1.500 | 1.500 | Flavor |
| Water | 68.870 | 68.870 | Solvent |

Sample Formulation 8

| Ingredient | % w/w | g/batch | Function |
|---|---|---|---|
| Xanthan Gum | 1.000 | 1.000 | Viscosity Builder |
| Poloxamer P407 | 18.000 | 18.000 | Gelling Agent |
| Glycerin | 10.000 | 10.000 | Humectant |
| Sucralose | 0.125 | 0.125 | Sweetener |
| SLS | 0.500 | 0.500 | Foaming |
| Green DB-110004 | 0.005 | 0.005 | Color - Dye Blend |
| Menthol | 0.500 | 0.500 | Flavor |
| Water | 69.870 | 69.870 | Solvent |

Sample Formulation 9

| Function | Ingredient | % w/w | g/batch |
|---|---|---|---|
| Viscosity Builder | Xanthan Gum | 1.000 | 1.000 |
| Gelling Agent | Poloxamer P407 | 18.000 | 18.000 |
| Humectant | Glycerin | 10.000 | 10.000 |
| sweetener | Sucralose | 0.125 | 0.125 |
| Foaming | SLS | 0.500 | 0.500 |
| Color - Dye Blend | Green DB-110004 | 0.005 | 0.005 |
| Flavor | Menthol | 0.750 | 0.750 |
| Solvent | Water | 69.620 | 69.620 |

While any of the above-listed sample formulations are useable in the beads or dabs 640, testing has revealed that sample formulation 8 and sample formulation 9, which include menthol as a flavorant at 0.50% w/w and 0.75% w/w, respectively, are potent, and can provide a strong burst of freshener, which can be desirable.

Although the beads 640 are depicted in the oral hygiene device 600, a person of skill in the art, guided by this disclosure, would understand that the beads 640 can be incorporated into any of the various embodiments of the oral hygiene device described herein. For example, the oral hygiene device 700 of FIGS. 7A-7K is also configured with beads, which are described in more detail below. As will be described below, the beads 640 may also comprise fluoride, iodine, or chlorohexidine, among other things. In some embodiments, the mouth wash or breath freshener can be applied to the device as a strip, rather than discrete beads. This may facilitate application on an assembly line by an automated process.

Figure 7A:
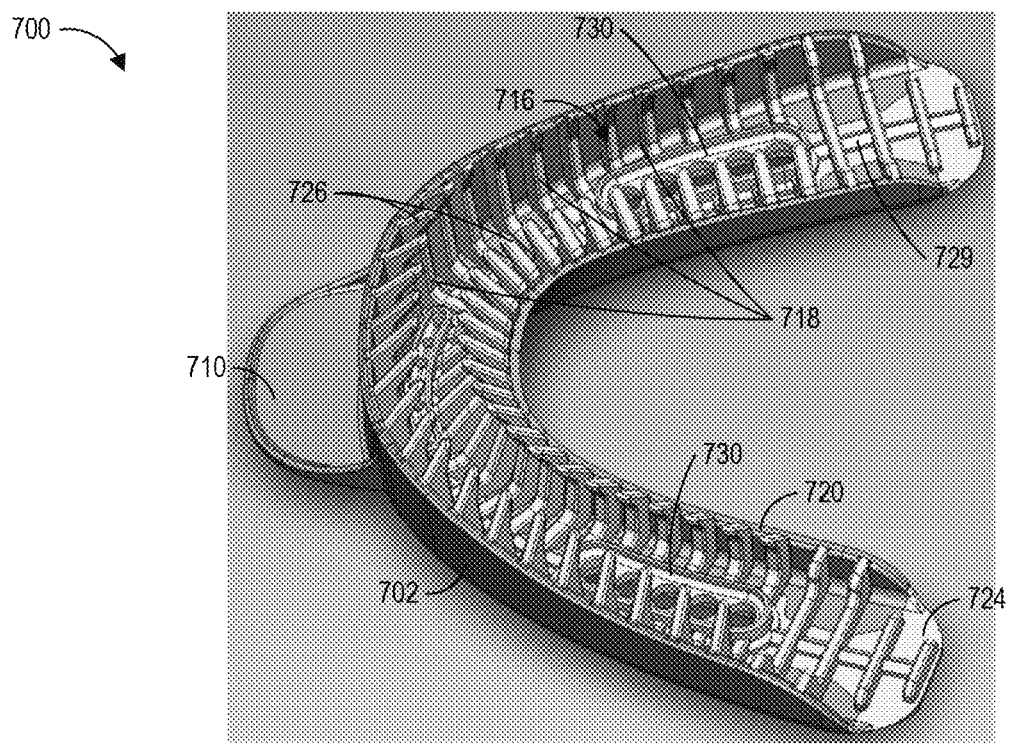
FIG. 7A is a top and side perspective view of another embodiment of an oral hygiene device.
Figure 7B:
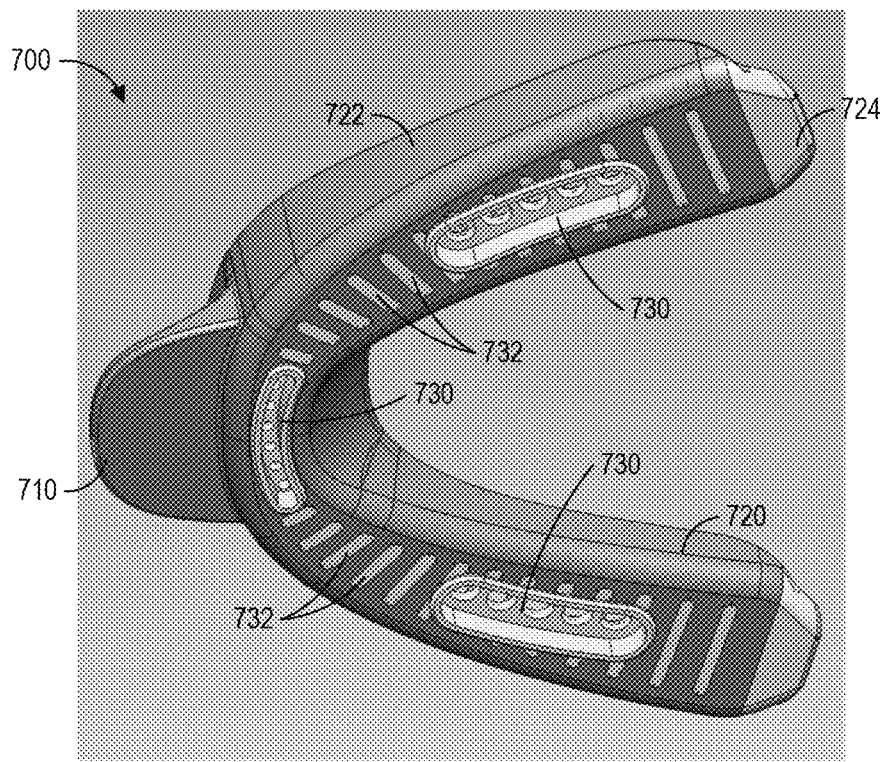
FIG. 7B is a bottom and side perspective view of the oral hygiene device of FIG. 7A.
Figure 7C:
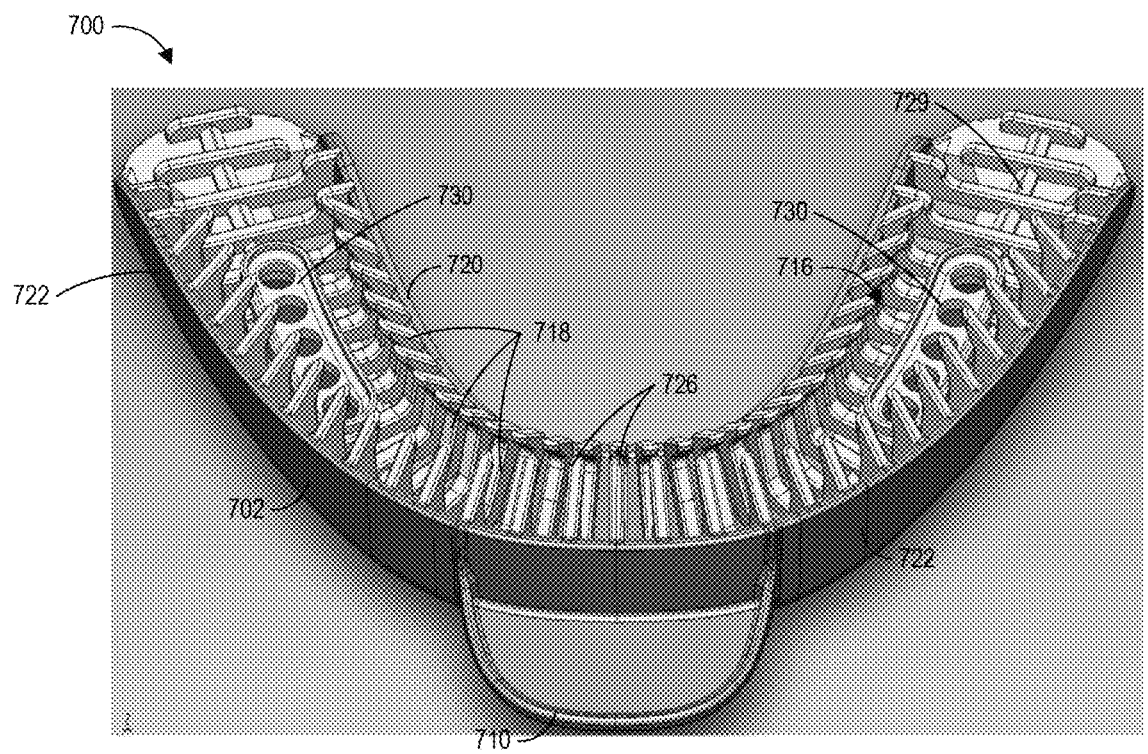
FIG. 7C is a top and front perspective view of the oral hygiene device of FIG. 7A.
Figure 7D:
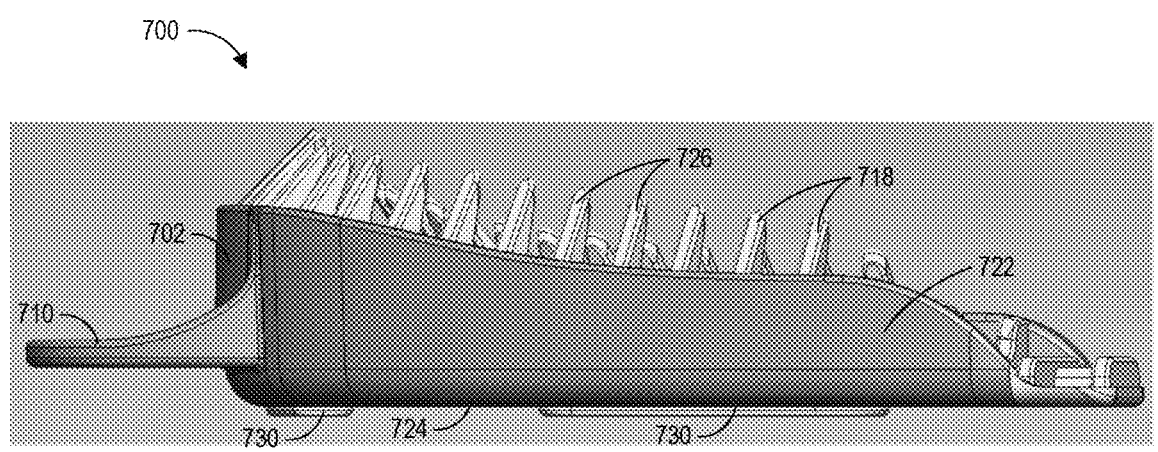
FIG. 7D is a side view of the oral hygiene device of FIG. 7A.
Figure 7E:
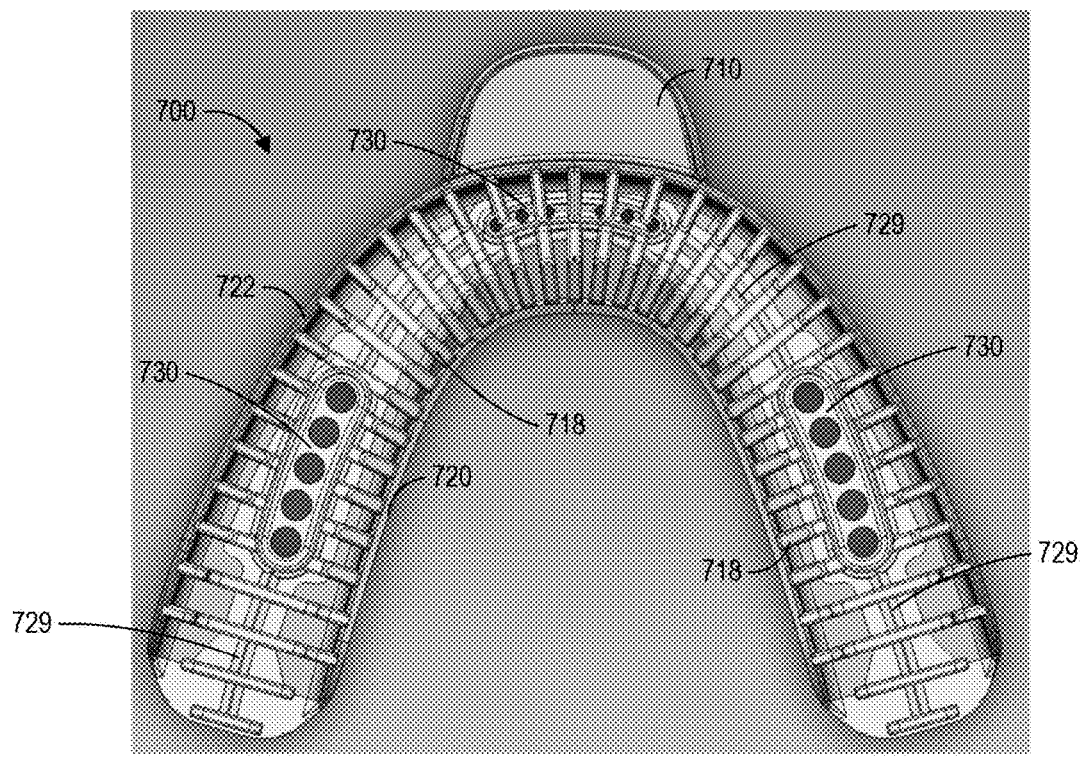
FIG. 7E is a top view of the oral hygiene device of FIG. 7A.
Figure 7F:
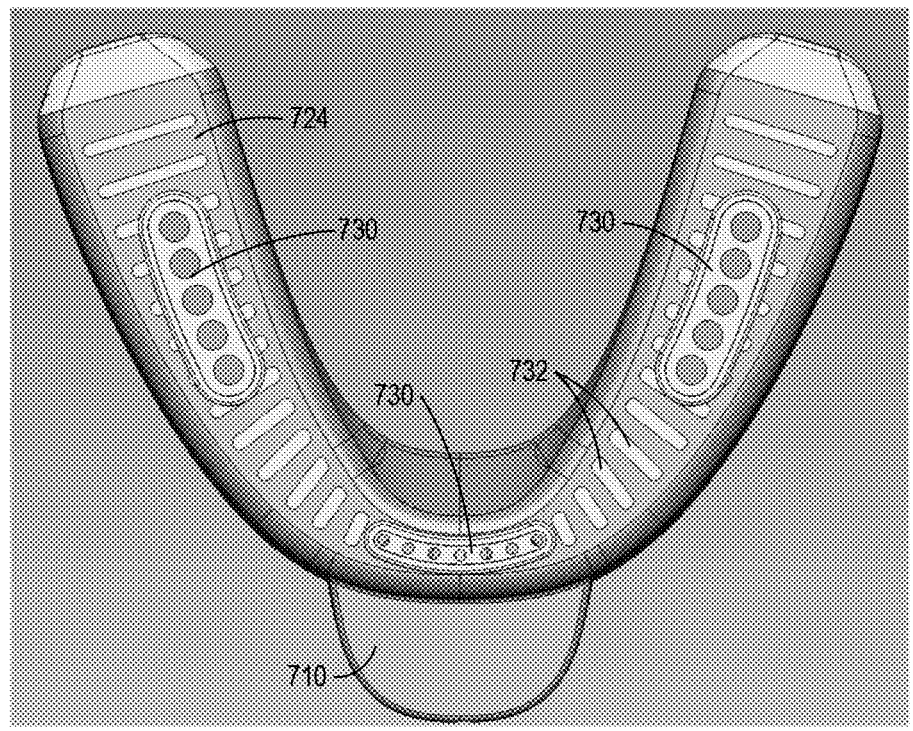
FIG. 7F is a bottom view of the oral hygiene device of FIG. 7A.
Figure 7G:
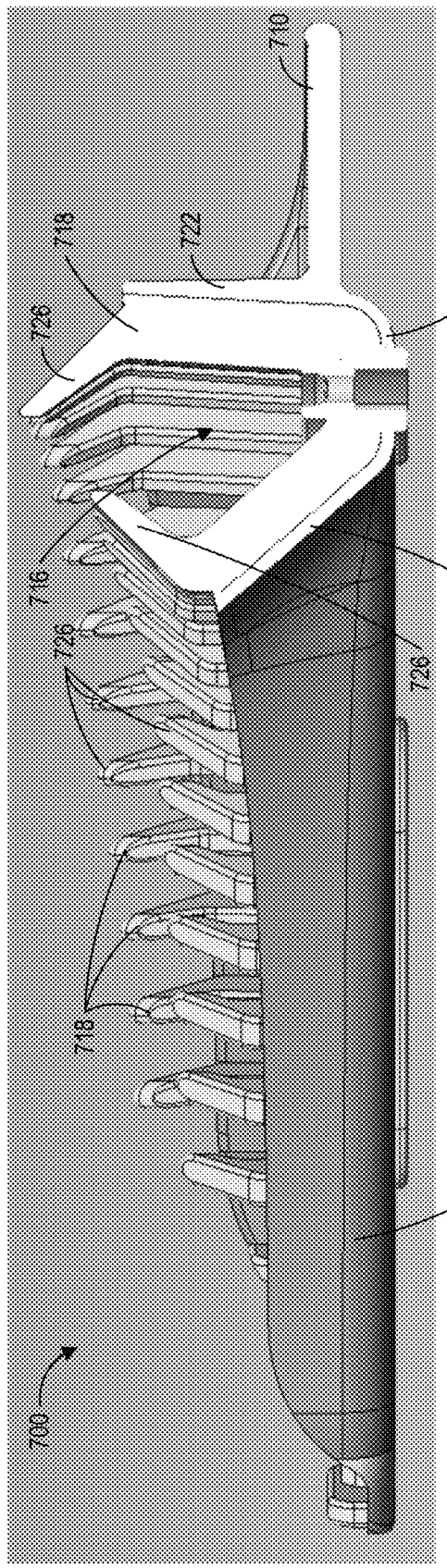
FIG. 7G is a first cross-sectional view of the oral hygiene device of FIG. 7A.
Figure 7H:
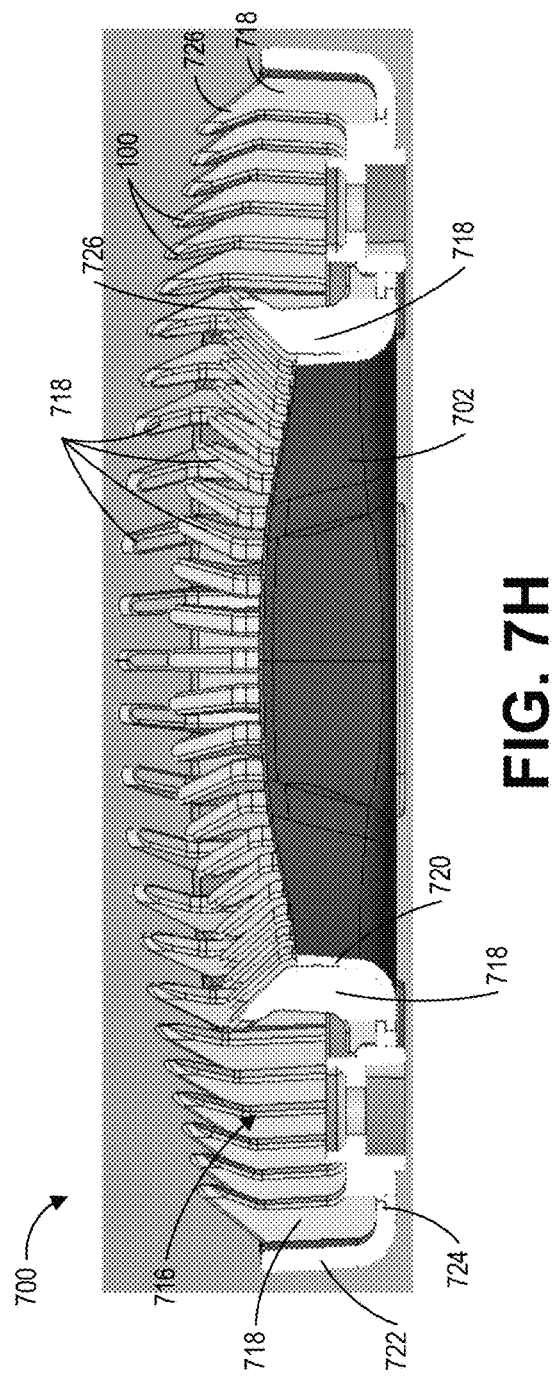
FIG. 7H is a second cross-sectional view of the oral hygiene device of FIG. 7A.
Figure 7I:
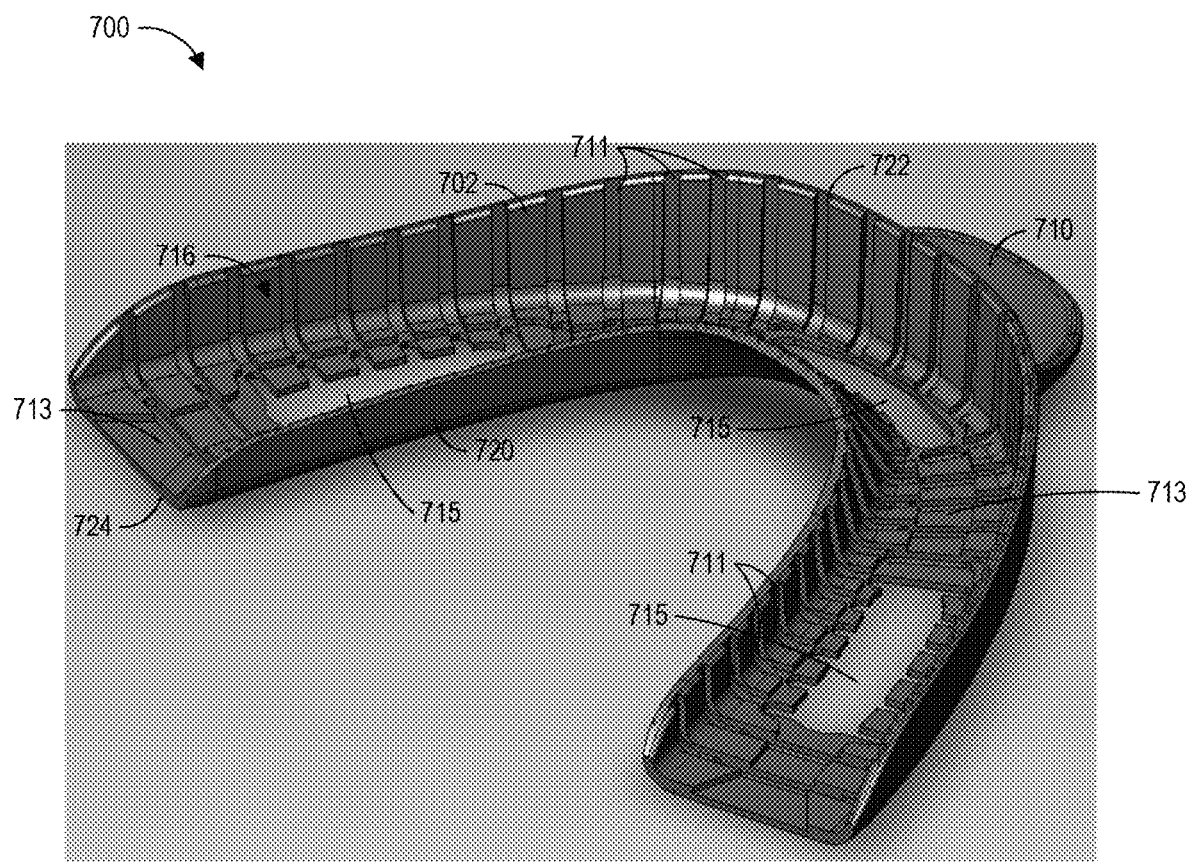
FIG. 7I illustrates a perspective view of the body of the oral hygiene device of FIG. 7A.
Figure 7J:
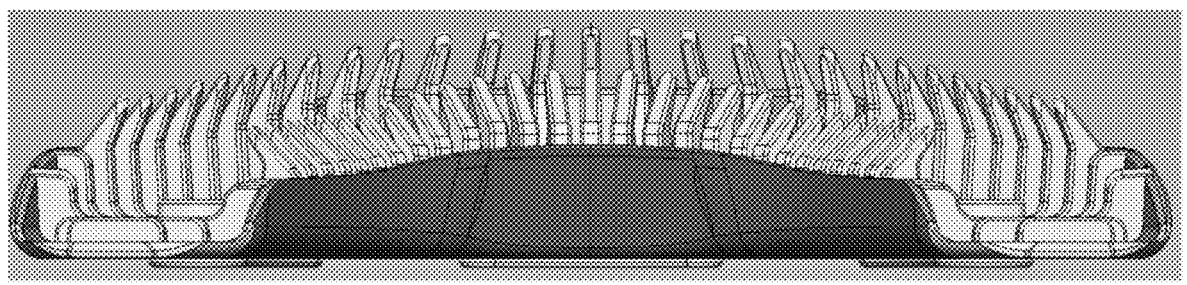
FIG. 7J is a back view of the oral hygiene device of FIG. 7A.
Figure 7K:
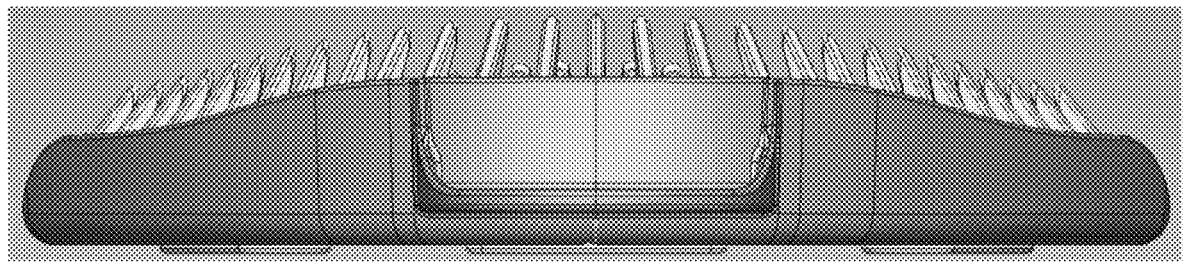
FIG. 7K is a front view of the oral hygiene device of FIG. 7A.

FIGS. 7A-7K illustrate views of another embodiment of an oral hygiene device 700. In some respects, the oral hygiene device 700 is similar to the oral hygiene device 100b shown in FIG. 1B, because the oral hygiene device 700 of FIGS. 7A-7I may similarly be configured for cleaning only the user's upper teeth or the user's lower teeth at a time. The oral hygiene device 700 can be used, for example, to clean the user's upper teeth and then can be flipped over and used to clean the user's lower teeth, or vice versa. FIG. 7A is a top and side perspective view, FIG. 7B is a bottom and side perspective view, FIG. 7C is a top and front perspective view, FIG. 7D is a side view, FIG. 7E is a top view, FIG. 7F is a bottom view, FIG. 7G is a first cross-sectional view, and FIG. 7G is a second cross-sectional view of the oral hygiene device 700. FIG. 7I illustrates a perspective view of the body 702 of the oral hygiene device 700. FIGS. 7J and 7K are back and front view so of the device 700.

With reference to FIGS. 7A-7I, the oral hygiene device 700 includes a body 702. The body 702 is shown alone in FIG. 7I and in FIGS. 7A-7H with additional teeth cleaning features molded there on. In the illustrated embodiment, the body 702 is generally U-shaped similar to the oral hygiene devices described previously. For example, the generally U-shaped body 702 can be configured to generally follow the shape of a user's upper and/or lower teeth. As illustrated, the body 702 also includes a generally U-shaped cross-sectional profile, similar to the oral hygiene devices 100b, 200 (and others) described above. The generally U-shaped cross-sectional profile may include an inner wall 720, an outer wall 722, and a bottom wall 724 as shown. The generally U-shaped cross-sectional profile can define a channel 716 within the body 702. The channel 716 can be formed between the inner wall 720 and the outer wall 722 and bounded below by the bottom wall 724. In some embodiments, the body 702 can be configured in size and shape such that the channel 716 is configured to receive the user's upper teeth or lower teeth during use of the oral hygiene device 700.

As shown in the cross-sectional views of FIGS. 7G and 7H, the shape of the channel 716 may vary at different positions of the body 702. For example, as shown in FIG. 7G, at the front of the body 702, the inner wall 720 may be formed at an angle with respect to the bottom wall 724. In some embodiments, the angle is between 30 and 60 degrees, between 40 and 50 degrees, or about 45 degrees. As shown, the outer wall 722 can extend at a substantially 90 degree angle (for example, 90 degrees plus or minus 5 or 10 degrees) with respect to the bottom wall 724. This shape allows the body 702 to fit comfortably over the user's front teeth, which generally comprises substantially vertical front surfaces and sloping, angled rear surfaces.

FIG. 7H is a cross-sectional view of the oral hygiene device 700 taken through a rear portion of the device. As shown, at this position, the both of the inner and outer walls 720, 724 are positioned at a substantially 90 degree angle (for example, 90 degrees plus or minus 5 or 10 degrees) with respect to the bottom wall 724. This shape can facilitate a good fit over the user's back teeth (e.g., molars), which are generally more rectangular in shape. Comparing FIGS. 7G and 7H, one can also see that, in the illustrated embodiment, the width of channel 716 can narrow from the rear of channel (FIG. 7H) toward the front of the channel (FIG. 7G). Again, this shape can facilitate fit with the user's teeth.

An additional feature that can facilitate good fit for the device 700 is visible in FIGS. 7G and 7H. As shown, the inner wall 720 can be shorter than the outer wall 722. This shape may be beneficial due to the anatomy of the mouth due to the upper palate, lower jaw, and tongue. In some instances, user's may experience pain or discomfort if the inner wall 720 and the outer wall 722 are the same height or if the inner wall 720 is too tall. Accordingly, in some embodiments, the inner wall 720 is less than 10 mm, less than 8 mm, less than 6 mm, less than 5 mm, or less than 4 mm tall. In some embodiments, the heights of inner wall 720 and the outer wall 722 can increase from the back towards the front of the body 702.

The body 702 may be made of a rigid, semi-rigid, or flexible material, such as plastic, rubber, a polymer, or other suitable material. In some embodiments, the body 702 is rigid enough to provide general support and shape for the oral hygiene device 700, while remaining flexible enough to allow the body 702 to fit to the particular anatomy of the user's mouth and teeth. In some embodiments, the body 702 comprises a thermoplastic elastomer (TPE), high-density polyethylene (HDPE), polypropylene (PP), low-density polyethylene (LDPE), polyamides, polyolefin or other resins, polychloro-trifluoroethylene, various thermoplastics, and/or various elastomers. In some embodiments, the body 702 may comprise a food grade polypropylene. The composition of the body 702 is not limited to the above materials, but is selected for specific characteristics including enough rigidity to provide general support and shape for the oral hygiene device 700, while including enough flexibility to allow the body 202 to fit to the particular anatomy of the user's mouth and teeth.

The body 702 may be formed such that the walls (e.g., the inner wall 720, the outer wall 722, and the bottom wall 724) are sufficiently thin so as to allow the body 702 to flex and conform to the shape of the user's mouth. For example, in some embodiments, the walls of the body 202 are about 2 mm, 1.5 mm, 1.0 mm, 0.75 mm, 0.5, or 0.25 mm thick. In some embodiments, the nominal thickness of the walls of the body 702 is about 1.2 mm. These thicknesses are provided by way of example, and the thickness of the walls of the body 702 can be selected to provide the desired characteristics described throughout this application.

FIG. 7I illustrates the body 702 alone. As shown in FIG. 7I, the body 702 can include a number of features formed within the channel 716 on the inner surfaces of the inner wall 720, the outer wall 720, and the bottom wall 724. As illustrated, the body 702 includes a plurality of grooves 711 formed within the channel. As illustrated, the grooves 711 can extend up and down the inner and outer walls 720 and along the bottom wall 724. The grooves 711 can be configured to receive the teeth cleaning features of the oral hygiene device 700, such as the ribs 718 described below. As such, the spacing of the grooves can be configured to match the spacing of the ribs 718 as will be described below. In some embodiments, for example, as illustrated, the body 702 may also comprise an indention 713 that extends along the inner surface of the bottom wall 724 as shown. The indention 713 can be configured to receive the spline 729, which is described below. FIG. 7I also illustrates that one or more apertures 715 can be formed through the bottom wall 724. As will be described below the apertures 715 can be configured to receive wells for holding beads or dabs of cleaning and/or freshening material.

In some embodiments, the oral hygiene device 700 can be provided in a variety of sizes (e.g., small, medium, large, adult, or child) configured for use by users that have different size mouths. In some embodiments, the oral hygiene device 700 can be provided in a size that is generally configured to fit most mouth sizes. For example, in some embodiments, the device 700 may comprise a width configured to fit mouths with a molar to molar width of about 50 mm to 65 mm, about 50 mm to 62 mm, about 52 mm to 58 mm, or about 54 mm to 56 mm. The device 700 may comprise a length configured to fit mouths with a front tooth to rear molar length of between 40 mm and 55 mm, between 40 and 50 mm, or between 43 and 49 mm. In some embodiments, the width of the device 700 is at least 62 mm. Measurements of many mouths were taken between the buccal of the second molar on the right and the buccal of the second molar of the left of the upper teeth. 62 mm was determined to be widest measurement.

As illustrated, the oral hygiene device 700 includes a handle 710. The handle 710 can be configured as a tab, although other shapes are possible as described in greater detail below (see, for example, FIGS. 17A-17D). The handle 710 can extend from a front portion of the body 702 so as to be able to extend out of the user's mouth between the user's lips when the oral hygiene device 700 is inserted into the user's mouth. In the illustrated embodiment, the handle 710 extends form the outer wall 722 of the body 702 at a position between the bottom wall 724 and the top of the outer wall 722. Alternatively, the handle 710 may be aligned with the bottom wall 724 of the body 702, or the handle 710 can be placed in any other desired location. In some embodiments, the oral hygiene device 700 does not include a handle 710 (i.e., the handle 710 may be omitted). Similar to the discussion above, the user may use the handle to manipulate the oral hygiene device 700 to use the oral hygiene device 700 to clean the user's teeth. In some embodiments, the handle 710 comprises a length of 11 mm and a width of 22 mm. However, other shapes of the handle 710 are also possible. For example, a longer handle 710 could be used that extends further out of the mouth. This may provide an easier hold for people with dexterity problems. This may also provide easier access to a caregiver using the device 700 on another person. For example, the caregiver may not have to put their fingers into the persons mouth.

Similar to the oral hygiene devices 100a, 100b, 200 (and others) described generally above, the oral hygiene device 700 can include teeth cleaning features configured to clean the user's teeth when the device is used. In the illustrated embodiment, the teeth cleaning features comprise the ribs 718, although in other embodiments, other types of teeth cleaning features (e.g., foam, bristles, textured surfaces, etc.) can be used in addition to or in place of the ribs 718.

The ribs 718 can be formed of the same material as the body 702, or the ribs 718 can be formed of a softer or more flexible material than the body 702 as described above. Advantageously, forming the body 702 and the ribs 718 of different materials may improve functionality, comfort, and efficiency of the device. For example, as described above the body 702 can be formed of a generally stiffer and more rigid material to provide structural support for the device 700, while the ribs 718 can be formed of a generally less rigid or softer material. The softer material of the ribs 718 can provide more user comfort during use, while also better conforming to the user's mouth and teeth shape to provide increased cleaning efficiency.

The ribs 718 can be integrally formed with the body 702 or can be separately formed and attached to the body 702. In some embodiments, the body 702 and ribs 718 are co-molded in a two-step molding process, such as a double shot or overmolding process, as described above. In other embodiments, the body 702 and the ribs 718 can be formed separately and then attached to one another. In some embodiments, the ribs 718 comprise a thermoplastic elastomer (TPE), silicon rubber, high-density polyethylene (HDPE), polypropylene (PP), low-density polyethylene (LDPE), polyamides, polychlorotrifluoroethylene, various thermoplastics, and/or various elastomers. In some embodiments, the ribs 718 comprise a food grade TPE or thermoplastic polyurethane (TPU). The composition of the ribs 718 is not limited to the above materials, but can be selected for specific characteristics including the ability to clean on and around teeth. In some embodiments, the ribs 718 may comprise a material with a Shore A hardness of between 70 and 100, between 75 and 95, or between 80 and 90, or between 85 and 90. Shore A hardnesses within these ranges can provide the comfort and efficiency advantages discussed above.

In the illustrated embodiment, the ribs 718 are positioned within the channel 716. In some embodiments, the shape of the ribs 718 can be formed in order to contour to a user's mouth and teeth. In some embodiments, the ribs 718 are about 1.2 mm, 1.0 mm, 0.8 mm, 0.6 mm, or 0.5 mm thick, although other thicknesses, both thinner and thicker than these example values are possible. The thickness can be selected to facilitate teeth cleaning efficiency and/or user comfort.

In some embodiments, the size and shape of the ribs 718 varies depending upon the location of the ribs 718 on the body 702. For example, the size and shape of the ribs 718 can be adjusted to suit the general size and shape of the particular teeth the ribs 718 will generally overlie when the oral hygiene device 700 is positioned within the mouth. Ribs 718 that are positioned on the body 702 to generally overlie molars (which are generally wider) may have a different shape than ribs 718 that are positioned to overlie incisors (which are generally thinner). The ribs 718 can also be configured such that they contact more than one surface of the user's teeth at a time. For example, the ribs 718 can be configured to contact the front, bottom and back surfaces of the user's upper teeth and/or the front, top, and back surfaces of the user's teeth simultaneously.

These features can be seen, for example, in the cross-sectional views of FIGS. 7H and 7G. As noted above, FIGS. 7G and 7H illustrate that the cross-sectional shape of the body 702 can vary from the back to the front of the device 700. As the ribs 718 are formed on the body 702, the shape of the ribs 718 can also vary from the back to the front. For example, as shown in FIG. 7G, the inner portion of the ribs 718 at the front of the device can be formed at an angle with respect to the bottom wall 724. In some embodiments, the angle is between 30 and 60 degrees, between 40 and 50 degrees, or about 45 degrees. As shown, an outer portion of the ribs 718 at the front of the device can extend at a substantially 90 degree angle (for example, 90 degrees plus or minus 5 or 10 degrees) with respect to the bottom wall 724. This shape can follow the shape of the channel 716 as described above and facilitate fit and user comfort. As shown in FIG. 7H, both the inner and outer portions of the ribs 718 at the rear of the device 700 can extend at a substantially 90 degree angle (for example, 90 degrees plus or minus 5 or 10 degrees) with respect to the bottom wall 724. Again, this shape follows the shape of the channel 716 and can provide good fit and comfort.

The ribs 718 may also have a shape that is adapted to clean the user's teeth, gums, and/or gum line. In the illustrated embodiment, the oral hygiene device 700 includes ribs 718 positioned within the channel 716. The ribs 718 positioned within the channel 716 can be configured to clean the upper and/or lower teeth of the user depending upon the orientation of the device 700. As illustrated, ribs 718 extend generally across the channel 716 from the inner wall 720 to the outer wall 722, as well as along the inner surfaces of the inner wall 720 and the outer wall 722. Such a configuration can allow the ribs to contact multiple surfaces of the user's teeth simultaneously as described above. In some embodiments, the shape of the individual ribs 718 may be varied to suit the particular teeth the ribs will contact during use. For example, as illustrated, the ribs 718 positioned within the back parts of the channel 716 (i.e., the ribs configured to clean molars) can have a wider cutout shape configured to match the thickness of the molars, and the ribs 718 positioned within the front part of the channel 716 (i.e., the ribs configured to contact incisors) have a narrower cutout shape configured to match the thickness of the incisors).

The one or more of the ribs 718 can include fingers 726 extending therefrom. The fingers 726 may be angled with respect to the gums so as to clean the space between the gums and the teeth. The fingers 726 be configured as protrusions or extensions that extend from the ribs 718. In some embodiments, the fingers 726 can be configured to clean the gum line. In some embodiments, the fingers 726 can be angled inwardly at an angle of between 30 and 60 degrees, between 40 and 50 degrees, or approximately 45 degrees with respect to the bottom wall 724, although other angles are also possible. The angle of the fingers 726 can be set in order to provide an optimal cleaning angle when the finger 726 contacts the teeth and/or the gum line (for example, as discussed above with regards to the Bass technique).

In some embodiments, the ribs 718 can be smaller or omitted at the rear ends of the oral hygiene device 700. For example, as shown in FIG. 7A, the last four ribs 718 on each end of the device 700 do not include the fingers 726. Thus, in the illustrated embodiment, the last four ribs 718 on each ends are smaller than the remaining ribs 718 on the device. In some embodiments, the ribs on the last 10 mm, 9 mm, 8 mm, 7 mm, 6 mm, or 5 mm of the device 700 can be smaller or omitted as shown. This can facilitate fit of the device 700 in the user's mouth and improve user comfort.

Moreover, in some embodiments, the rear most portions of the device 700 can be made from the same material as the ribs 718. Thus, the rearmost portions can be softer than body 702. For example, comparing FIGS. 7A and 7B to FIG. 7I, one can see that the rear most portions of the device 700 can extend beyond the rear most portions of the body 702. This can facilitate user comfort and accommodate different size mouths.

In the illustrated embodiment, the oral hygiene device 700 includes about 35 ribs in the channel 716, although other numbers are possible (e.g., about 15, about 20, about 25, about 30, about 35, about 40, about 45, or about 50 ribs 718). The ribs 718 may be spaced evenly or unevenly. In some embodiments, the ribs 718 are spaced apart so as to be aligned with the spaces between the user's teeth or the interproximal contact area (IPC) when the oral hygiene device 700 is inserted into the mouth. In some embodiments, there can be more ribs 718 disposed in the channel 716 than there are upper teeth. This can provide additional coverage for teeth cleaning and can reduce the amount a user would need to move the oral hygiene device 700 in order to contact and adequately clean all the teeth. In some embodiments, the ribs 718 are spaced about 2 mm, 4 mm, 6 mm, 8 mm, or 10 mm apart, although other spacings are possible. The position and spacing of the ribs 718 can be selected to facilitate operation of the device. For example, the ribs 718 can be positioned so as to efficiently clean the teeth. In some embodiments, the spacing of the ribs 718 is a function of the average dimensions of each tooth.

The ribs 718 positioned within the channel 716 may be connected by a spline 729 as shown, for example, in FIG. 7E. The spline 729 can be configured to clean the occlusal surface of the teeth. The spline 729 can be positioned within the channel 716 on the bottom wall 724. In some embodiments, the spline 729 runs continuously from one end of the channel 716 to the other. The shape, size, materials, and placement of the spline 729 can be based on specific desirable characteristics, such as the ability to clean the occlusal surface of each tooth. The spline 729 may interconnect the ribs 718. The spline 729 can be formed from the same material as the ribs 718.

The oral hygiene device 700 may also include reservoirs 730 for holding beads or dabs of a cleaning or freshening material as described above. In the illustrated embodiment, the device 700 includes three reservoirs 730 that extend through the apertures 715 of the body 702. As shown, one reservoir 730 is positioned at the front of the device 700 and the remaining two reservoirs 730 are positioned toward the rear of the device 700. These positions for the reservoirs 730 may work well to release the material of the dabs or beads over the much or all of the user's mouth or teeth and provide good coverage. Other numbers of reservoirs 730 and other positions for the reservoirs 730 are also possible. The reservoirs 730 can be formed from the same material as the spline 729 and the ribs 718. As shown in the figures, in some embodiments, the reservoirs 730 extend above and below the bottom wall 724. This may facilitate release of the bead or dab material. For example, in some embodiments, the reservoirs 730 may extend at least 0.5 mm, at least 1.0 mm, or at least 1.5 mm above and/or below the body 702.

As illustrated, in some embodiments, the reservoirs 730 can include within them one or more openings that extend therethrough. The openings may facilitate release of the bead or dab material both above and below the device 700 during use. In the illustrated embodiment, the front reservoir 730 includes six openings, while the rear two reservoirs 730 can include five openings. The size and number of the openings through the reservoirs 730 can be configured to release of the bead or dab material.

As shown in FIGS. 7B and 7F, the device 700 can include tongue cleaning features formed on the bottom surface of the bottom wall 724. As illustrated, the tongue cleaning features can comprise ridges 732 that project slightly downward from the bottom wall 724. The ridges 732 can extend downwardly from the bottom wall 724 of the body 702. In some embodiments, the ridges 732 extend at least 0.25 mm, at least 0.5 mm, at least 0.75 mm, at least 1.0 mm, at least 1.25 mm, at least 1.5 mm, or at least 2.0 mm below the bottom wall 724 of the body 702. The ridges 732 can be configured to scrape and/or clean the user's tongue as will be described in more detail below. The ridges 732 can be formed of the same material as the ribs 718. Although the tongue cleaning features are illustrated as ridges 732 in FIGS. 7A-7H, other tongue cleaning features can also be used in other embodiments.

The oral hygiene device 700 can be configured to be used to clean and/or freshen a user's mouth, teeth, and tongue. An example method of use for the device 700 will now be described. In this example, the device 700 can be inserted into the user's mouth. The user may hold the device 700 using the handle 710. The device 700 can be inserted into the mouth such that the user upper or the user's lower teeth are positioned within the channel 716. For example, the user's upper teeth can be positioned within the channel 716. With the device 700 so positioned, the user may manipulate the device 700 to freshen the mouth. For example, the user may manipulate the device 700 by moving the device 700 side-to-side and back-and-forth. During this motion, the ribs 718 can contact and clean the surfaces of the user's teeth. At the same time the fingers 726 can contact and clean the user's gum line. The motion can produce similar effects as the Bass technique described above. Further, while using the device, the dab and bead material device can be naturally released, providing additional cleaning and/or freshening for the mouth.

In some embodiments, while cleaning the user's upper teeth, the teeth cleaning features (ridges 732) of the bottom wall 724 of the device 700 can clean the user's tongue. This can be accomplished by moving the ridges 732 across the surface of the user's tongue. Advantageously, the bead or dab material can be released from the reservoir 730 onto the user's tongue providing additional freshening.

After the user's upper teeth and tongue are cleaned, the user can flip the device 700, such that the user's lower teeth are received within the groove 716. The device can then be used in a similar manner to clean the user's lower teeth. In some embodiments, the user's lower teeth can be cleaned first, before cleaning the user's upper teeth.

Figure 8:
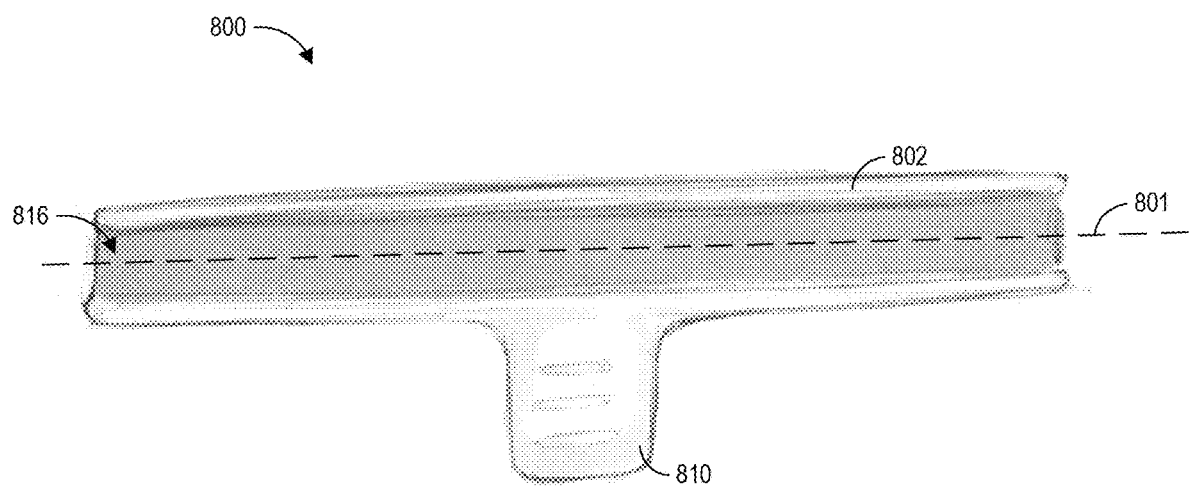
FIG. 8 is a top view of an embodiment of a formable oral hygiene device that is initially generally straight, but can be formed into a U-shape during use to fit to a user's teeth.

FIG. 8 is a top view of an embodiment of a formable oral hygiene device 800 that is initially generally straight, but can be formed into a U-shape during use to fit to a user's teeth. In some embodiments, instead of including hinges as described above with reference to FIGS. 3A-4B, the formable oral hygiene device 800 can be provided. As shown in FIG. 8, the formable oral hygiene device 800 can include a body 800 that initially extends generally linearly along an axis 801. This shape may be advantageous for storage, for example, within a long slender container, as shown in FIGS. 5A-5C. As illustrated in FIG. 8, the body 802 of the device also includes a channel 816 (which can include teeth cleaning features) and can have an H-shaped cross-section (see FIG. 1A) or U-shaped cross-section (see FIG. 1B). In the illustrated embodiment, the formable oral hygiene device 800 includes a handle 810 as shown.

The body 802 can be made of a flexible material, or otherwise configured to bend or flex, so that the user can form the formable oral hygiene device 800 into a U-shape when inserting the device 800 into the user's mouth. The U-shape will conform the formable oral hygiene device 800 to the general shape of the user's mouth and teeth. The user may then use the formable oral hygiene device 800 in the manner previously described. FIGS. 8-13B illustrate several embodiments of formable oral hygiene devices.

Figure 9A:
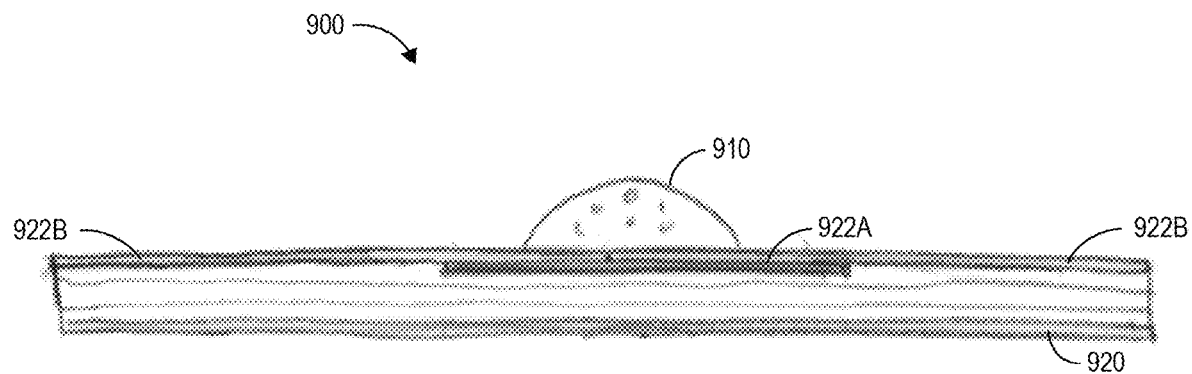
FIGS. 9A and 9B illustrates top views of another embodiment of an oral hygiene device including at least some portions that are formable in a straight configuration and a bent configuration, respectively.
Figure 9B:
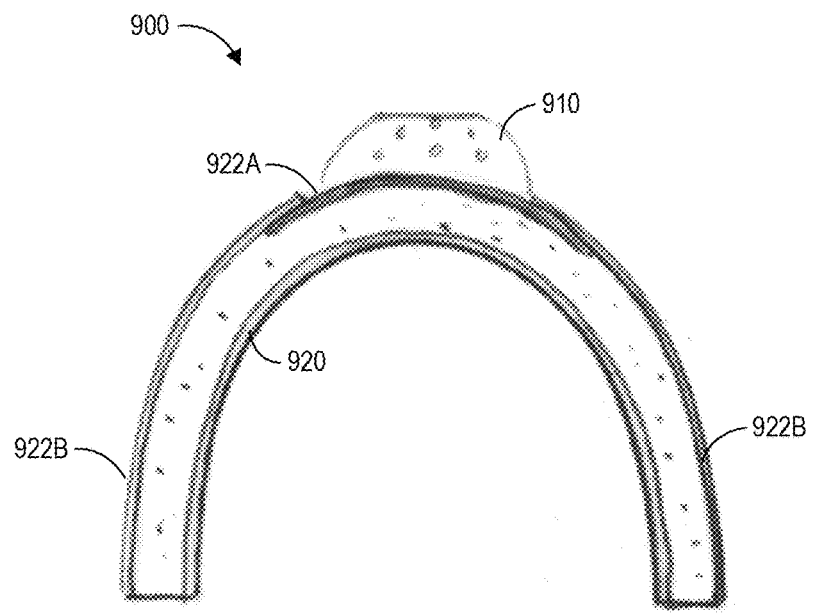

FIGS. 9A and 9B illustrate views of another embodiment of a formable oral hygiene device 900. To accommodate bending formable oral hygiene device 900 from a generally linear shape (FIG. 9A) to a general U-shape (FIG. 9B), the device 900 includes an outer wall 922 formed by three discrete portions 922A, 922B. In the linear configuration, the two portions 922B contact each other and the portion 922A is positioned inside of the two portions 922B. As the device 900 is bent to the U-shaped configuration, the ends of the two portions 922B move apart, exposing the portion 922A. Thus, in the linear configuration, the outer wall comprises the two portions 922B, and in the U-shaped configuration, the outer wall comprises the portion 922A and the two portions 922B. This allows the outer wall to increase in length to accommodate the bend. In the U-shaped configuration, the outer wall will have a larger radius than the inner wall, and thus, in this embodiment, must have a longer length.

Figure 10A:
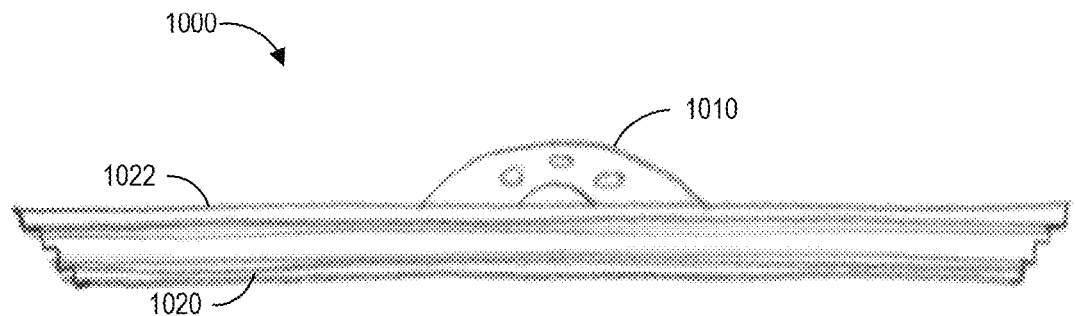
FIGS. 10A and 10B illustrate views of another embodiment of an oral hygiene device including at least some portions that are formable in a straight configuration and a bent configuration, respectively.
Figure 10B:
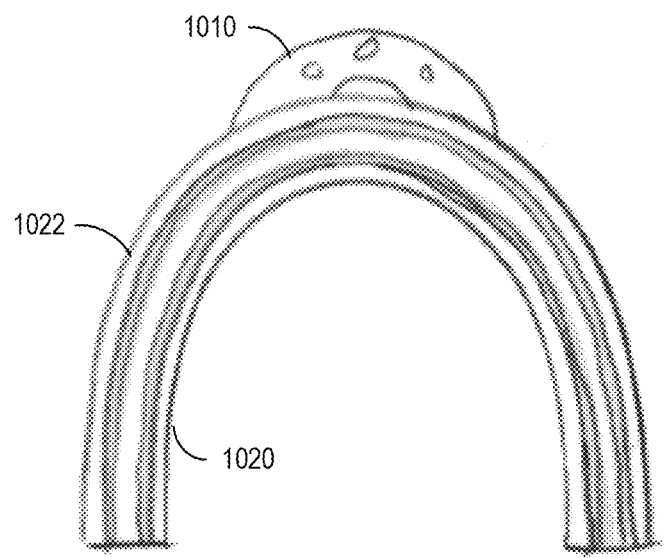

FIGS. 10A and 10B illustrate views of another embodiment of a formable oral hygiene device 1000. In this embodiment, the body of the formable oral hygiene device 1000 comprises a plurality of laminated layers. As shown, outermost layers can comprise a longer length than the innermost layers to accommodate the larger radius of the outer wall 1022 in the U-shaped configuration (FIG. 10B). Accordingly, in this embodiment, the outer wall 1022 may be formed of a longer layer and the inner wall 1020 may be formed of a shorter layer.

Figure 11A:
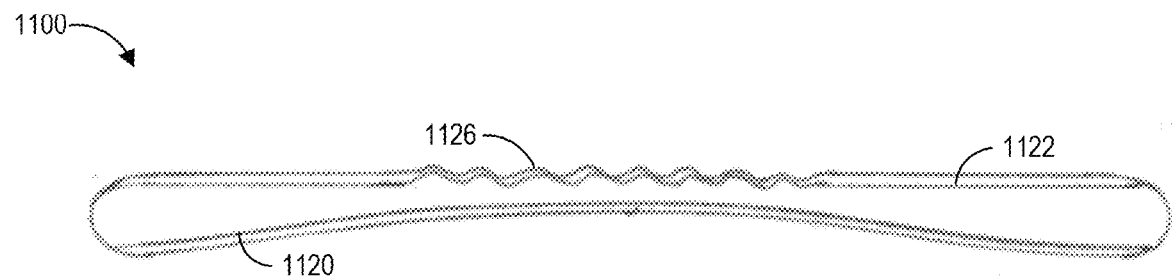
FIGS. 11A and 11B illustrate views of another embodiment of an oral hygiene device including at least some portions that are formable in a straight configuration and a bent configuration, respectively.
Figure 11B:
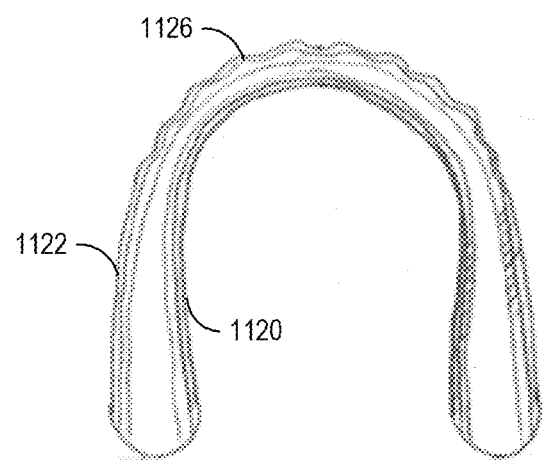

FIGS. 11A and 11B illustrate views of another embodiment of a formable oral hygiene device 1100. In this embodiment, the outer wall 1122 includes a corrugated portion 1126, which allows the length of the outer wall 1122 to increase as the device 1100 is bent to the U-shaped configuration. The length and shape of the outer wall 1122 (including the corrugated portion 1126) and the inner wall 1120 can be configured such that a thickness between the outer wall 1122 and the inner wall 1120 matches an approximate thickness of the teeth when the device 1100 is bent into the U-shaped configuration. For example, the thickness can be narrower in areas that fit incisors and wider in areas that fit molars.

Figure 12A:
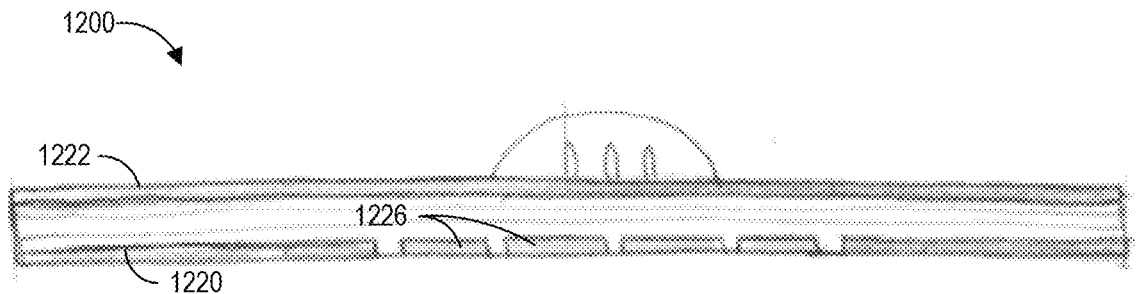
FIG. 12A, 12B, 12C illustrate views of another embodiment of an oral hygiene device including at least some portions that are formable.
Figure 12B:
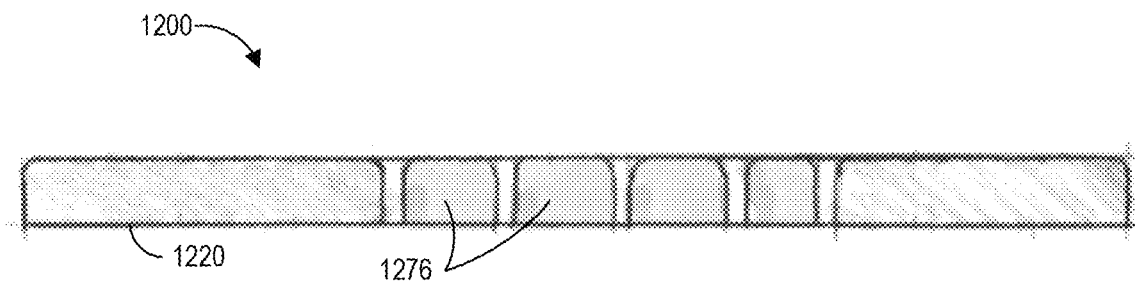
Figure 12C:
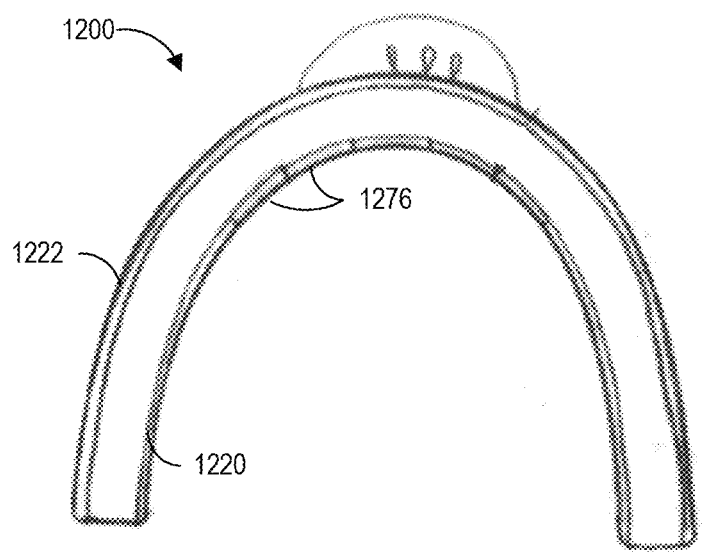

FIGS. 12A-12C illustrate views of another embodiment of a formable oral hygiene device 1200. As mentioned above, in the U-shaped configuration, the outer wall 1222 comprises a longer length (because of the larger radius) than the inner wall 1220. To accommodate this, the formable oral hygiene device 1200 includes an inner wall 1220 that includes a plurality of dentils, teeth, or tabs 1276. The tabs can be positioned on the inner wall 1220 in an area of high flex. In the linear configuration, the tabs 1276 are separated by gaps. When bent into the U-shaped configurations, the gaps between the tabs 1276 close up as shown.

Figure 13A:
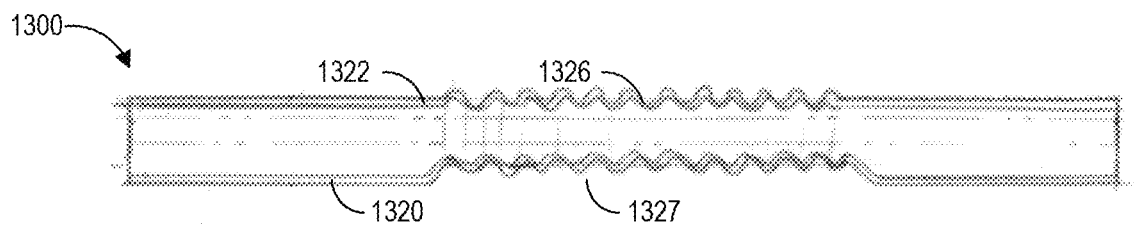
FIGS. 13A and 13B illustrate views of another embodiment of an oral hygiene device including at least some portions that are formable in a straight configuration and a bent configuration, respectively.
Figure 13B:
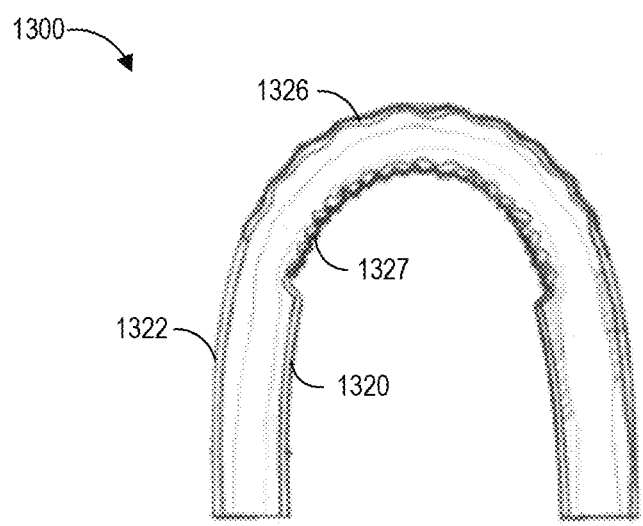

FIGS. 13A and 13B illustrate views of another embodiment of a formable oral hygiene device 1300. The formable oral hygiene device 1300 is in some respects similar to the formable oral hygiene device 1100 (FIGS. 11A and 11B) described above. For example, the formable oral hygiene device 1300 includes an outer surface 1322 with a corrugated portion 13726. However, the formable oral hygiene device 1300 also includes an inner surface 1320 with a corrugated portion 1327.

FIGS. 14A-14D illustrate various embodiments for handles that can be used to manipulate the oral hygiene devices described herein. The various handles illustrated in these figures can be included on any of the oral hygiene device described above. Other types of handles are also usable. In general, the handle allows the user to manipulate the device (e.g., move the device back and forth and/or up and down) to clean the user's teeth.

Figure 14B:
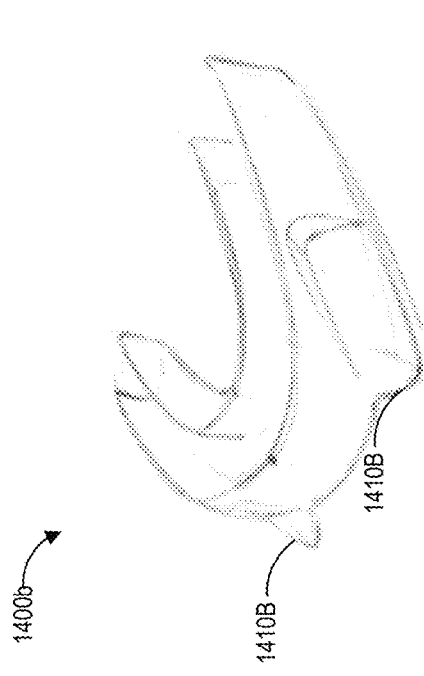
FIG. 14B is a perspective view illustrating an embodiment of an oral hygiene device that includes two handles.
Figure 14D:
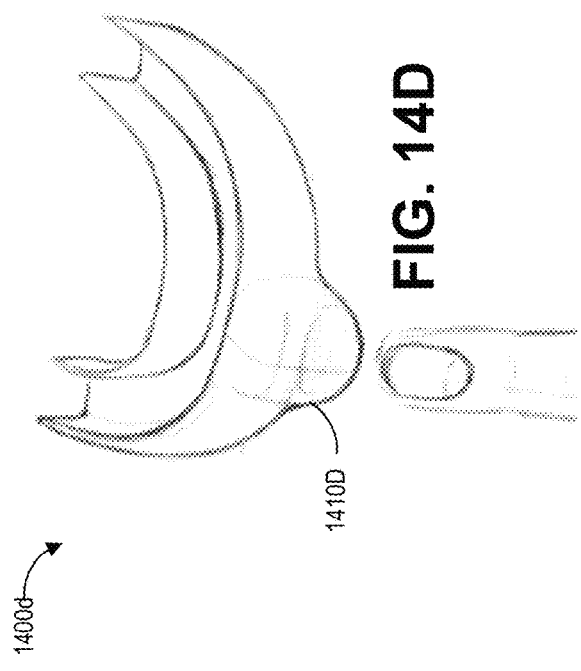
FIG. 14D is a perspective view of an oral hygiene device illustrating another embodiment of a handle for the device.
Figure 14A:
FIG. 14A is a perspective view illustrating an embodiment of a handle for an oral hygiene device.

FIG. 14A is a perspective view illustrating an embodiment of a handle 810A for an oral hygiene device 1400a. In the illustrated embodiment, the handle 1410a is a tab positioned on the front of the device as previously described.

FIG. 14B is a perspective view illustrating an embodiment of an oral hygiene device 1400b that includes two handles 1410B. Each handle 1410B can be positioned on an opposite side of the device 1400b. In some embodiments, the user uses a handle 1410B on one side to focus on cleaning the teeth on the corresponding side and then transitions to using the other handle 1410B on the other side to focus on cleaning the teeth on the other side.

Figure 14C:
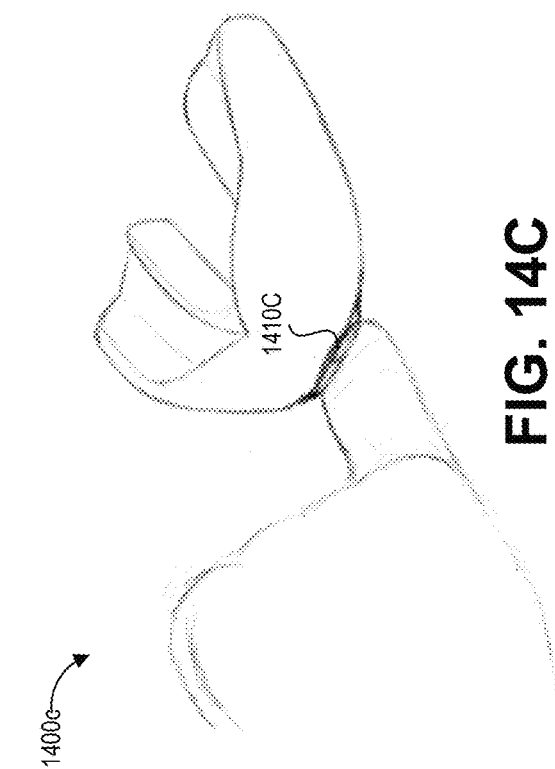
FIG. 14C is a perspective view illustrating an embodiment of an oral hygiene device that includes a contact point configured for manipulation of the device.

FIG. 14C is a perspective view illustrating an embodiment of an oral hygiene device 1400c that includes a contact point 1410C configured for manipulation of the device. In this embodiment, rather than including a handle, the device 1400c includes a contact point 1410C that the user contacts to manipulate the device. The contact point 1410C may include a high-friction material or surface to prevent the user user's finger from slipping off of the contact point. In some embodiments, the user contacts the contact point with the thumb to press upwards to clean the top teeth and then uses a different finger (e.g., the index finger) to press down to clean the bottom teeth.

FIG. 14D is a perspective view of an oral hygiene device 800d illustrating another embodiment of a handle 1410D for the device. In this embodiment, the handle comprises a recess or loop into which the user inserts a finger to manipulate the device. The axis of insertion can be either normal to the plane of the device or parallel to the plane of the device.

Figure 15:
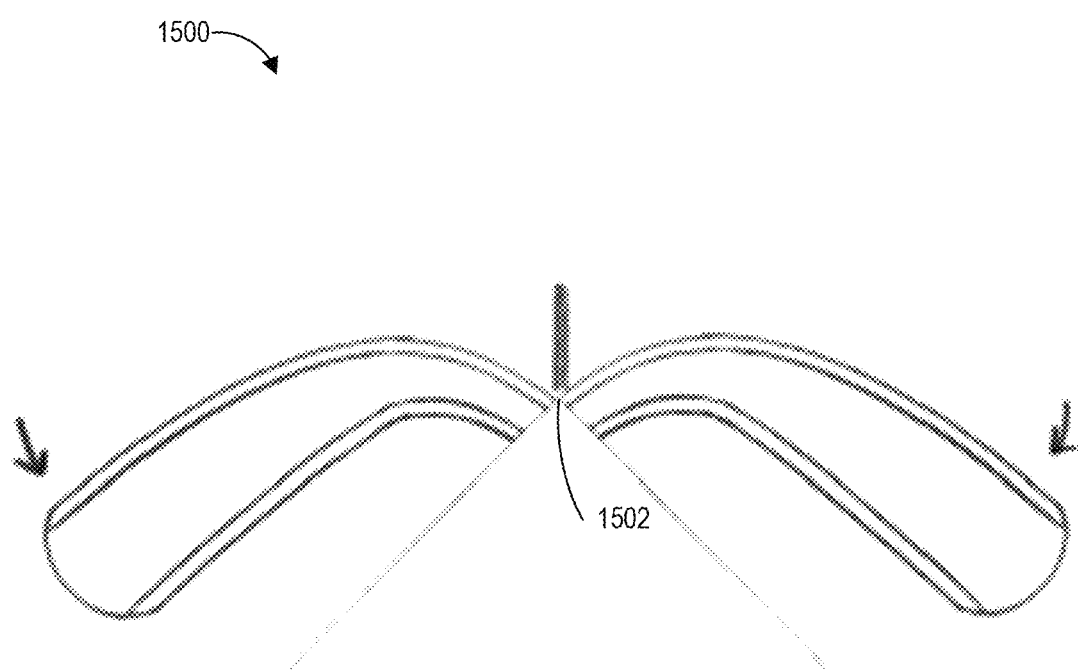
FIG. 15 is a top view of an embodiment of an oral hygiene device that includes a single hinge.

FIG. 15 is a top view of an embodiment of an oral hygiene device 900 that includes a single hinge 1502. In some embodiments, the device 1500 includes a single hinge 1502, rather than the dual hinges 402 previously described with reference to FIGS. 3A-4B. The single hinge 1502 can be positioned at the front of the device 1500. The single hinge 1502 can be a living hinge or a mechanical hinge. In some embodiments, the device 1500 also includes a locking mechanism to secure the device 1500 in the closed configuration.

Figure 16A:
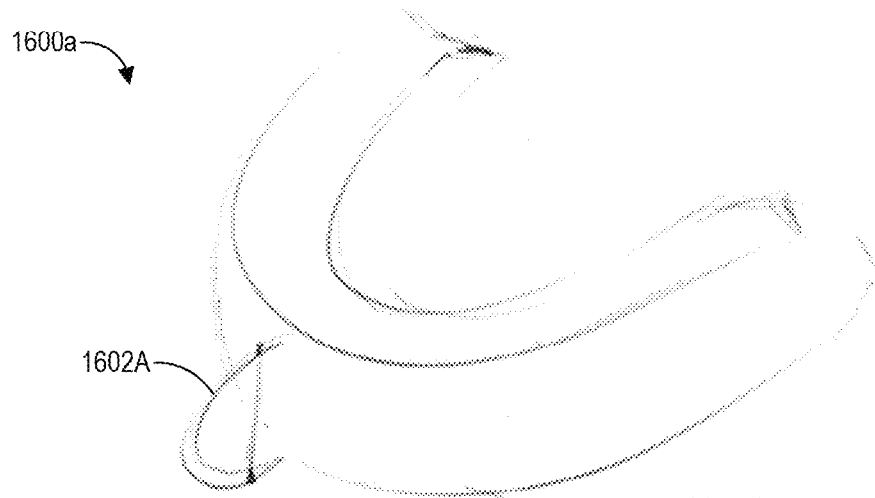
FIG. 16A is a perspective view of an embodiment of an oral hygiene device that includes a removable floss device that can also be used as a handle for the device.

FIG. 16A is a perspective view of an embodiment of an oral hygiene device 1600a that includes a removable floss device 1602A that can also be used as a handle for the device. In the illustrated embodiment, the removable floss device 1602A is positioned at the front of the device 1600a. The removable floss device 1602A comprises a C-shaped body that is connected to the body of the device 1600a. The C-shaped body is strung with floss. The removable floss device 1602A can be gripped by the user to manipulate the device 1000a during cleaning. Afterwards, the user may remove the removable floss device 1602A and use it to floss between teeth as desired.

Figure 16B:
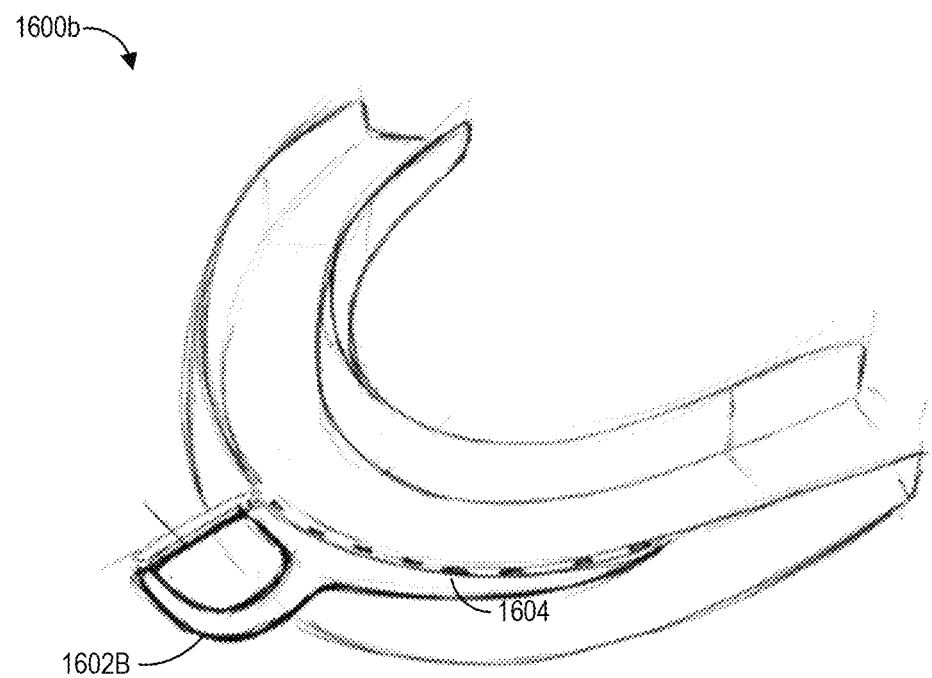
FIG. 16B is a perspective view of another embodiment of an oral hygiene device that includes a removable floss device that can also be used as a handle for the device.

FIG. 16B is a perspective view of another embodiment of an oral hygiene device 1600b that includes a removable floss device 1602B that can also be used as a handle for the device. The removable floss device 1602B is similar to the removable floss device 1600A described above, except that the removable floss device 1602B includes an elongated handle portion 1604 that can be used to hold the removable floss device 1602B after it has been removed.

Figure 17B:
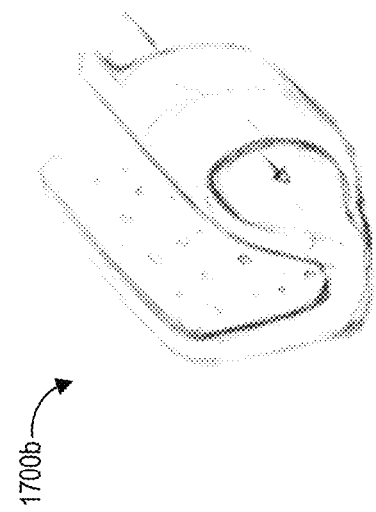
FIG. 17B illustrates a perspective view of another embodiment of a U-shaped oral hygiene device that includes a handle configured to receive a finger.
Figure 17D:
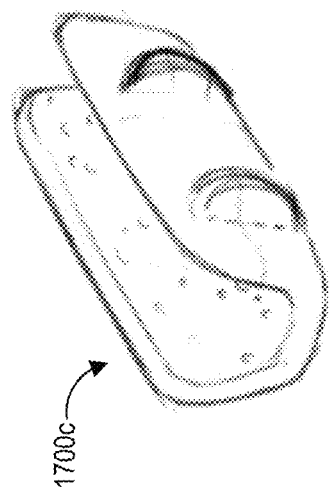
FIG. 17D illustrates a perspective view of an embodiment of a U-shaped oral hygiene device that includes dual handles.
Figure 17A:
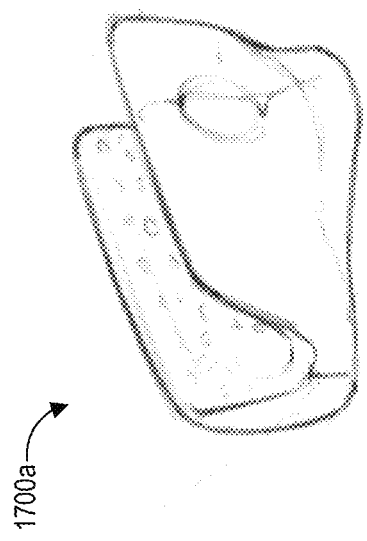
FIG. 17A illustrates a perspective view of an embodiment of a U-shaped oral hygiene device.

FIGS. 17A-17D illustrate oral hygiene devices that are configured to clean both sides (front and back) of the teeth, but do not clean all of the teeth at once as with the previously described oral hygiene devices. FIG. 17A illustrates a perspective view of an embodiment of a U-shaped oral hygiene device 1700a. The device is described as U-shaped because it has a U-shaped cross-section. The U-shaped cross-section can include a body having channel formed therein. The channel can include teeth cleaning features as described above.

FIG. 17B illustrates a perspective view of another embodiment of a U-shaped oral hygiene device 1700b that includes a handle configured to receive a finger.

Figure 17C:
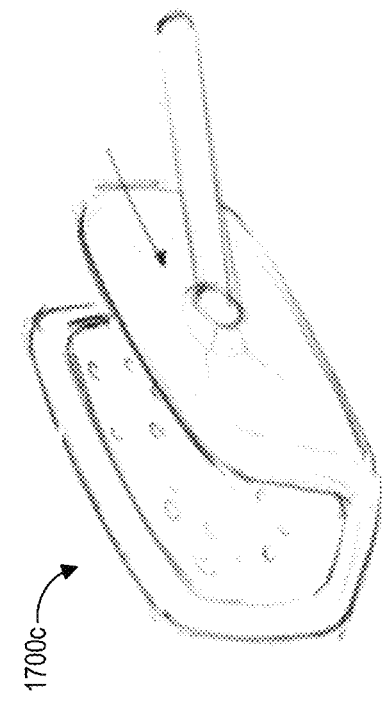
FIG. 17C illustrates a perspective view of another embodiment of a U-shaped oral hygiene device that includes a handle attached to the device by a joint.

FIG. 17C illustrates a perspective view of another embodiment of a U-shaped oral hygiene device 1700c that includes a handle attached to the device by a joint. The handle can comprise a rod extending from the joint. The rod can be sufficiently long that the user does not need to reach his or her fingers into the mouth to manipulate the device. In some embodiments, the joint is a ball joint.

FIG. 17D illustrates a perspective view of an embodiment of a U-shaped oral hygiene device 1700d that includes dual handles.

The oral hygiene device described herein can be used to clean teeth and/or freshen the mouth as described above. In some embodiments, the devices can be used as a supplement to a traditional tooth care routine, which generally involves twice daily brushing. For example, the devices can be used on-the-go, in between brushings, as a supplement to improve oral healthcare. In some embodiments, this is facilitated by the fact that the devices can be configured to be useable without requiring access to water and/or a bathroom. In addition, by reducing or eliminating the need for people to find public restrooms while on-the-go to clean their teeth, people can avoid the unsanitary conditions associated with public restrooms (such as the spread of germs and other unsanitary material due to toilet plume).

In some embodiments, the devices can be configured to provide fluoride as means to prevent tooth decay. The Global Burden of Disease Study from 2016 estimated that oral diseases affected half of the world's population (3.58 billion people) with dental caries (tooth decay) in permanent teeth being the most prevalent condition assessed. Poor oral hygiene and inadequate exposure to fluoride can have negative effects on oral health. Further, oral health is a key indicator of overall health, wellbeing and quality of life. The World Health Organization (WHO) defines oral health as "a state of being free from chronic mouth and facial pain, oral and throat cancer, oral infection and sores, periodontal (gum) disease, tooth decay, tooth loss, and other diseases and disorders that limit an individual's capacity in biting, chewing, smiling, speaking, and psychosocial wellbeing."

Additionally, poor oral health can be even more common in developing countries, with increasing urbanization and changes in living conditions. The prevalence of oral diseases continues to increase notably due to inadequate exposure to fluoride and poor access to primary oral health care services. Heavy marketing of sugars, tobacco and alcohol also leads to growing consumption of unhealthy products.

Dental caries results when microbial biofilm (plaque) formed on the tooth surface converts the free sugars contained in foods and drinks into acids that dissolve tooth enamel and dentine over time. With continued high intake of free sugars, inadequate exposure to fluoride and without regular microbial biofilm removal, tooth structures are destroyed, resulting in development of cavities and pain, impacts on oral-health-related quality of life, and, in the advanced stage, tooth loss and systemic infection.

The burden of oral diseases and other non-communicable diseases (NCDs) can be reduced through public health interventions by addressing common risk factors. In addition, to the NCDs' common risk factors, inadequate exposure to fluoride and a number of social determinants of health should be addressed to prevent oral diseases and reduce oral health inequalities.

Dental caries can be largely prevented by maintaining a constant low level of fluoride in the oral cavity. Optimal fluoride can be obtained from different sources such as fluoridated drinking water, salt, milk and toothpaste. Twice-daily tooth brushing with fluoride-containing toothpaste (1000 to 1500 ppm) should be encouraged, although people often fail to use adequate fluoride. Long-term exposure to an optimal level of fluoride results in substantially lower incidence and prevalence of tooth decay across all ages. Accordingly, the devices described herein can be used as a supplement for applying fluoride. This is even more true for developing areas were access to water is not available.

In some embodiments, the devices can be configured to provide a dose of fluoride of approximately 1000-1500 ppm. This dose of fluoride can be include in the device, but would have to be spit out and cannot be swallowed. It may be in the dabs or beads or dispensed in another mode, such as paste coated within the channel of the device. This can greatly improve dental health in areas where access to water is limited. This may be especially helpful for children (especially since an estimated 486 million children suffer from tooth decay).

The oral hygiene devices of the present application may also be especially useful for people with limited mobility. For example, because the device are configured to clean substantially all the teeth at once, they may require less dexterity than a traditional toothbrush. Further, the devices can be used by caretakers who are cleaning the teeth of another person, such as a person in a nursing home. Use of the device can be particularly advantageous because caretaker can use the device without having to place their fingers into the persons mouth. This can reduce the time required to clean the persons teeth and freshen the mouth and clean the tongue leading to better health outcomes for the residents and better social interactions.

While the above detailed description has shown, described, and pointed out novel features of the development as applied to various embodiments, it will be understood that various omissions, substitutions, and changes in the form and details of the device or process illustrated may be made by those skilled in the art without departing from the spirit of the development. As will be recognized, the present development may be embodied within a form that does not provide all of the features and benefits set forth herein, as some features may be used or practiced separately from others. All changes which come within the meaning and range of equivalency of the claims are to be embraced within their scope.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present development. This development is susceptible to modifications in the methods and materials, as well as alterations in the fabrication methods and equipment. Such modifications will become apparent to those skilled in the art from a consideration of this disclosure or practice of the development disclosed herein. Consequently, it is not intended that this development be limited to the specific embodiments disclosed herein, but that it cover all modifications and alternatives coming within the true scope and spirit of the development.

What is claimed is:

1. An oral hygiene device comprising:
    a U-shaped body comprising a first material, the U-shaped body comprising a channel configured to receive a user's upper or lower teeth, the channel comprising an inner wall, a bottom wall, and an outer wall, wherein the inner wall and the outward wall extend from the bottom wall to form the channel;
    teeth cleaning features over molded onto the U-shaped body, the teeth cleaning features made of a second material that is softer than the first material and the teeth cleaning features comprising:
        a plurality of ribs disposed within the channel, at least some of the ribs comprising:
            a lower portion formed on the bottom wall of the channel between the inner wall and the outer wall, wherein the lower portion extends upwardly from the bottom wall,
            an outer extension portion formed on an inner surface of the outer wall and connected to the lower portion, wherein the outer extension portion extends inwardly from the inner surface of the outer wall, and wherein an outer finger extends from the outer extension portion above the outer wall at an angle of approximately 45 degrees with respect to the bottom wall of the channel, the finger pointing away from the bottom wall and the outer wall of the channel, and
            an inner extension portion formed on an inner surface of the inner wall and connected to the lower portion, wherein the inner extension portion extends inwardly from the inner surface of the inner wall, and wherein an inner finger extends from the inner extension portion above the inner wall at an angle of approximately 45 degrees with respect to the bottom wall of the channel, the finger pointing away from the bottom wall and the inner wall of the channel,
            wherein the outer and inner fingers are configured in size and shape to contact at least a portion of an outer and inner gumline during use of the oral hygiene device;
    one or more reservoirs holding a dab configured to freshen the user's mouth, wherein the dab is configured to be useable without water;
    wherein the oral hygiene device is configured to be useable without access to water or a restroom.

2. The oral hygiene device of claim 1, wherein the first material comprises polypropylene, and wherein the second material comprises a thermoplastic elastomer (TPE) or a thermoplastic polyurethane (TPU).

3. The oral hygiene device of claim 1, wherein the second material comprises a Shore A hardness between 80 and 90.

4. The oral hygiene device of claim 1, further comprising one or more tongue cleaning features extending from a bottom surface of the bottom wall of the channel of the body.

5. The oral hygiene device of claim 4, wherein the one or more tongue cleaning features comprise one or more ridges formed of the second material.

6. The oral hygiene device of claim 1, wherein the one or more reservoirs are configured to extend through the bottom wall of the U-shaped body.

7. The oral hygiene device of claim 6, wherein the one or more reservoirs are configured to extend at least 0.5 mm above and below the bottom wall of the U-shaped body.

8. The oral hygiene device of claim 7, wherein the one or more reservoirs comprise openings extending therethrough to facilitate release of the dab.

9. The oral hygiene device of claim 1, wherein the dab comprises a formulation that is safe to swallow.

10. The oral hygiene device of claim 1, wherein the dab comprises fluoride.

11. The oral hygiene device of claim 1, wherein the one or more teeth cleaning features are configured to contact at least 50%, at least 60%, at least 75%, at least 80%, or at least 90% of the user's upper or lower teeth simultaneously.

12. The oral hygiene device of claim 1, further comprising a handle extending from the U-shaped body.

13. A method for freshening or cleaning a user's mouth, the method comprising:
    inserting an oral hygiene device into a user's mouth, the oral hygiene device comprising: a U-shaped body comprising a first material, the U-shaped body comprising a channel configured to receive a user's upper or lower teeth, the channel comprising an inner wall, a bottom wall, and an outer wall, wherein the inner wall and the outward wall extend from the bottom wall to form the channel;
    teeth cleaning features over molded onto the U-shaped body, the teeth cleaning features made of a second material that is softer than the first material and the teeth cleaning features comprising:

a plurality of ribs disposed within the channel, at least some of the ribs comprising:
- a lower portion formed on the bottom wall of the channel between the inner wall and the outer wall, wherein the lower portion extends upwardly from the bottom wall,
- an outer extension portion formed on an inner surface of the outer wall and connected to the lower portion, wherein the outer extension portion extends inwardly from the inner surface of the outer wall, and wherein an outer finger extends from the outer extension portion above the outer wall at an angle of approximately 45 degrees with respect to a bottom wall of the channel, the finger pointing away from the bottom wall and the outer wall of the channel, and
- an inner extension portion formed on an inner surface of the inner wall and connected to the lower portion, wherein the inner extension portion extends inwardly from the inner surface of the inner wall, and wherein an inner finger extends from the inner extension portion above the inner wall at an angle of approximately 45 degrees with respect to a bottom wall of the channel, the finger pointing away from the bottom wall and the inner wall of the channel, wherein the outer and inner fingers are configured in size and shape to contact at least a portion of an outer and inner gumline during use of the oral hygiene device;

one or more reservoirs holding a dab configured to freshen the user's mouth, wherein the dab is configured to be useable without water;

wherein the oral hygiene device is configured to be useable without access to water or a restroom;

positioning the oral hygiene device such that the user's upper or lower teeth are positioned within the channel;

moving the oral hygiene device side to side and front to back to clean the user's upper or lower teeth, wherein moving the oral hygiene device distributes a formulation from the dab in the one or more reservoirs of the oral hygiene device;

flipping the oral hygiene device such that the other of the user's upper or lower teeth are positioned within the channel; and moving the oral hygiene device side to side and front to back to clean the other of the user's upper or lower teeth.

14. The method of claim 13, wherein the method is performed without access to water or a restroom.

15. The method of claim 13, further comprising cleaning the user's tongue with one or more tongue cleaning features of the oral hygiene device by running the one or more tongue cleaning features of the oral hygiene device over the tongue.

16. The method of claim 13, wherein the oral hygiene device is configured to contact at least 50%, at least 60%, at least 75%, at least 80%, or at least 90% of the user's upper or lower teeth simultaneously.

17. The method of claim 13, further comprising disposing of the oral hygiene device after use.

18. The method of claim 13, further comprising swallowing the formulation, and wherein the formulation is safe to swallow.

19. The method of claim 13, wherein the formulation comprises fluoride.

* * * * *